US010005793B2

(12) United States Patent
Mazitschek et al.

(10) Patent No.: US 10,005,793 B2
(45) Date of Patent: Jun. 26, 2018

(54) BODIPY DYES FOR BIOLOGICAL IMAGING

(71) Applicant: The General Hospital Corporation, Boston, MA (US)

(72) Inventors: Ralph Mazitschek, Belmont, MA (US); Alexandra M. Courtis, Davis, CA (US); James Adam Hendricks, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days. days.

(21) Appl. No.: 14/432,567

(22) PCT Filed: Oct. 1, 2013

(86) PCT No.: PCT/US2013/062850
§ 371 (c)(1),
(2) Date: Mar. 31, 2015

(87) PCT Pub. No.: WO2014/055505
PCT Pub. Date: Apr. 10, 2014

(65) Prior Publication Data
US 2015/0252061 A1   Sep. 10, 2015

Related U.S. Application Data

(60) Provisional application No. 61/708,894, filed on Oct. 2, 2012, provisional application No. 61/708,277, filed on Oct. 1, 2012.

(51) Int. Cl.
| C07F 5/02 | (2006.01) |
|---|---|
| C07D 257/08 | (2006.01) |
| G01N 33/534 | (2006.01) |
| A61K 51/04 | (2006.01) |

(52) U.S. Cl.
CPC ............ C07F 5/02 (2013.01); A61K 51/0446 (2013.01); C07D 257/08 (2013.01); C07F 5/025 (2013.01); G01N 33/534 (2013.01)

(58) Field of Classification Search
CPC .................................. C07F 5/02; C07F 5/025
USPC .......... 548/405; 544/179; 435/7.1; 424/1.89, 424/9.6
See application file for complete search history.

(56) References Cited

U.S. PATENT DOCUMENTS

| 6,106,999 A | 8/2000 | Ogiso et al. |
|---|---|---|
| 2005/0249668 A1 | 11/2005 | Weissleder et al. |
| 2009/0176313 A1 | 7/2009 | Suzuki et al. |
| 2011/0287473 A1 | 11/2011 | De Berry et al. |

FOREIGN PATENT DOCUMENTS

JP    11-043491    2/1999

OTHER PUBLICATIONS

Pimlott SL., Nucl. Med. Commun. 26(3): 183-188, 2005; PubMed Abstract provided.*
Smithen et al. J. Org. Chem. 2012, 77, 3439-3453.*
Ehrenschwender et al. Nucleic Acids Symposium Series (2008), 52(1), 349-350; CA 150: 369191, 2008. CAPLUS Abstract provided.*
Ogiso et al. JP 2002236360, Aug. 23, 2002; CA 137: 192756, 2002. CAPLUS Abstract provided.*
Nakagawa et al. JP 2002169275, Jun. 14, 2002; CA 137: 39315, 2002. CAPLUS Abstract provided.*
Taizo et al. JP 2000029213, Jan. 28, 2000; CA 132: 130023, 2000. CAPLUS Abstract provided.*
Imai et al. JP 20000003038, Jan. 7, 2000; CA 132: 85909, 2000. CAPLUS Abstract provided.*
Nishimoto et al. JP 11322744, Nov. 24, 1991; CA 132: 7580, 1999. CAPLUS Abstract provided.*
International Preliminary Report on Patentability in International Application PCT/US2013/062850, dated Apr. 7, 2015, 12 pages.
Blom, et al., "Preparative LC-MS Purification: Improved Compound-Specific Method Optimization," J Comb Chem. Nov.-Dec. 2004;6(6):874-83.
Devaraj and Weissleder, "Biomedical applications of tetrazine cycloadditions," Acc Chem Res., Sep. 20, 2011;44(9):816-27 (Author Manuscript).
Haun et al., "Bioorthogonal chemistry amplifies nanoparticle binding and enhances the sensitivity of cell detection," Nat Nanotechnol., 2010, 5(9):660-665 (Author Manuscript).
Hendricks et al., "Synthesis of [18F]BODIPY: bifunctional reporter for hybrid optical/positron emission tomography imaging," Angew Chem Int Ed Engl., May 7, 2012;51(19):4603-6 (Author Manuscript).
Hudnall and Gabbi, "A BODIPY boronium cation for the sensing of fluoride ions," Chem Commun (Camb)., Oct. 14, 2008;(38):4596-7.
Berge et al., "Pharmaceutical Salts," J Pharm Sci., Jan. 1977;66(1):1-19.
Loudet and Burgess, "BODIPY dyes and their derivatives: syntheses and spectroscopic properties," Chem Rev., Nov. 2007;107(11):4891-932.

(Continued)

*Primary Examiner* — Venkataraman Balasubramanian
(74) *Attorney, Agent, or Firm* — Fish & Richardson P.C.

(57) ABSTRACT

This invention relates to water-soluble mono-alkoxy and mono-alkyne BODIPY derivatives, including methods for making the same. For examples, provided herein are compounds of Formula (I): (I) or a pharmaceutically acceptable salt thereof, wherein: (a) is a BODIPY ligand system; X is a halogen; L is absent or a linker; and Z is selected from the group consisting of: a group reactive with a biologically active molecule and a detectable agent.

(I)

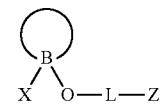

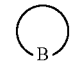

(a)

8 Claims, 6 Drawing Sheets

(56) References Cited

OTHER PUBLICATIONS

Peturssion et al., "Protecting Groups in Carbohydrate Chemistry," J Chem. Educ., 74(11):1297-1303 (1997).
Ravin, "Perforrnulation," Remington's Pharmaceutical Sciences, 17th ed., 1985, pp. 1409-1418.
Reiner et al., "Synthesis and in vivo imaging of a 18F-labeled PARP1 inhibitor using a chemically orthogonal scavenger-assisted high-performance method," Angew Chem Int Ed Engl., Feb. 18, 2011;50(8):1922-5 (Author Manuscript).
Sletten and Bertozzi, "Bioorthogonal chemistry: fishing for selectivity in a sea of functionality," Angew Chem Int Ed Engl., 2009;48(38):6974-98 (Author Manuscript).
Tahtaoui et al., "Convenient method to access new 4,4-dialkoxy- and 4,4-diaryloxy-diaza-s-indacene dyes: Synthesis and spectroscopic evaluation," J Org Chem., Jan. 5, 2007;72(1):269-72.
Ulrich et al., "The chemistry of fluorescent bodipy dyes: versatility unsurpassed," Angew Chem Int Ed Engl., 2008;47(7):1184-201.
Wang et al., "Small-molecule reagents for cellular pull-down experiments," Bioconjug Chem., Mar. 2008;19(3):585-7.
Yang et al., "Live-cell imaging of cyclopropene tags with fluorogenic tetrazine cycloadditions," Angew Chem Int Ed Engl., Jul. 23, 2012;51(30):7476-9 (Author Manuscript).
Ziessel et al., "The chemistry of Bodipy: A new El Dorado for fluorescence tools," New J Chem., 2007, 31:496-501.
International Search Report and Written Opinion dated Feb. 27, 2014 in international application No. PCT/US2013/062850, 7 pgs.

* cited by examiner

BODIPY DYES FOR BIOLOGICAL IMAGING

CROSS-REFERENCE TO RELATED APPLICATIONS

This application is a U.S. National Phase Application under 35 U.S.C. § 371 of International Patent Application No. PCT/US2013/062850, filed on Oct. 1, 2013, which claims priority to U.S. Provisional Application Ser. No. 61/708,277, filed on Oct. 1, 2012, and U.S. Provisional Application Ser. No. 61/708,894, filed on Oct. 2, 2012, all of which are incorporated by reference herein in their entireties.

FEDERALLY SPONSORED RESEARCH OR DEVELOPMENT

This invention was made with Government support under Grant Nos. P50A086355 and T32-CA079443 awarded by the National Cancer Institute. The Government has certain rights in the invention.

TECHNICAL FIELD

This invention relates to water-soluble mono-alkoxy and mono-alkyne BODIPY derivatives, including methods for making the same. Also provided herein are methods of using the derivatives provided herein for biomedical imaging.

BACKGROUND

Fluorescently labeled small molecules are an important class of probes for studying biology. Tethering fluorophores to compounds of interest can allow for visualizing reversible and temporal perturbations of biological systems in their endogenous state. From these agents, real-time information can be gathered on a compound's cellular localization as well as other indicators such as the quantitative expression levels of an intended target. In the field of chemical biology, the synthesis of such tagged, small molecules has been fruitful, allowing for the exploration of critical modes of action in disease states. These fluorescent probes have also served an equally pivotal role in the mechanistic exploration of promising clinical candidates and established chemotherapies.

Selection of the organic fluorophore for these small molecules is a central aspect of probe development. While there are many commercially available dyes, only a few can be used for chemical biology, and even from this select pool, many suffer from at least one key drawback. A fluorophore for imaging in chemical biology has a particular ideal target profile and should possess a specific set of attributes. Of primary importance is the brightness of the dye. This is a quantifier that allows for side-by-side comparison of different fluorophores and is defined as the product of the quantum yield and the extinction coefficient. Additionally, the fluorophore should have good aqueous solubility while retaining a favorable partition coefficient (log P value). An appropriate balance of these two factors is important to ensure that the dye can diffuse through membranes and organelles easily while concurrently engaging in minimal, non-specific membrane staining. Tied with these attributes is the necessity of the dye to remain a neutral, uncharged species in aqueous environments. Finally, the fluorophore should demonstrate long-term stability to aqueous and cellular imaging media, minimal consumption of chemical space, and a modular functional group for bioconjugate chemistry. The premise of these stipulations is the need for the fluorophore to maintain chemical stability with ideal optical properties in the cell while contributing minimal drug-like attributes that would interfere with the visualization and mechanism of the probe of interest.

SUMMARY

The difluoro-boron-dipyrromethene dyes (BODIPYs) are a class of compounds that fulfills many of the parameters for a fluorophore outlined above. BODIPYs are fluorescent because of a highly compact boron dipyrromethene core and boast admirably high quantum yields. They are non-ionizable which contributes to their robust stability and also allows for easy diffusion/passage across cell membranes. Importantly, their absorption and emission profiles can be tuned via accessible chemistry on the carbon core skeleton. Unfortunately, the core fluorophore of these dyes is inherently lipophilic and causes the dye to engage in non-specific staining of membranes and intracellular organelles. In addition, these core fluorophores have the propensity to aggregate and precipitate out of aqueous solutions.

Provided herein are mono-fluoro alkyoxy and mono-fluoro alkyne BODIPY derivatives and methods for making the same. These derivatives are highly water-soluble, possess low lipophilicity, and maintain the optical properties of the parent difluoro-BODIPY dye class. A diverse array of different derivatives can be easily accessed via a one-pot synthetic strategy that allows for the selective exchange of a fluorine on the boron core of the dye with a single alkoxy or alkyne bearing ligand. From a technical standpoint, the disclosed synthesis method allows for the direct modification of the boron core of the BODIPY fluorophore with a solubilizing ligand and/or useful functional groups for bioconjugate and bioorthogonal chemistries.

This disclosure provides, for example, a compound of Formula (I):

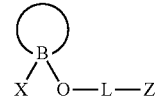

or a pharmaceutically acceptable salt thereof, wherein:

is a BODIPY ligand system;
X is a halogen;
L is absent or a linker; and
Z is selected from the group consisting of: a group reactive with a biologically active molecule and a detectable agent.

In some embodiments, the moiety O-L-Z is selected from the group consisting of:

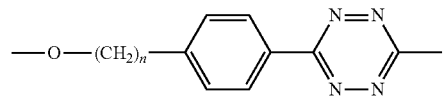

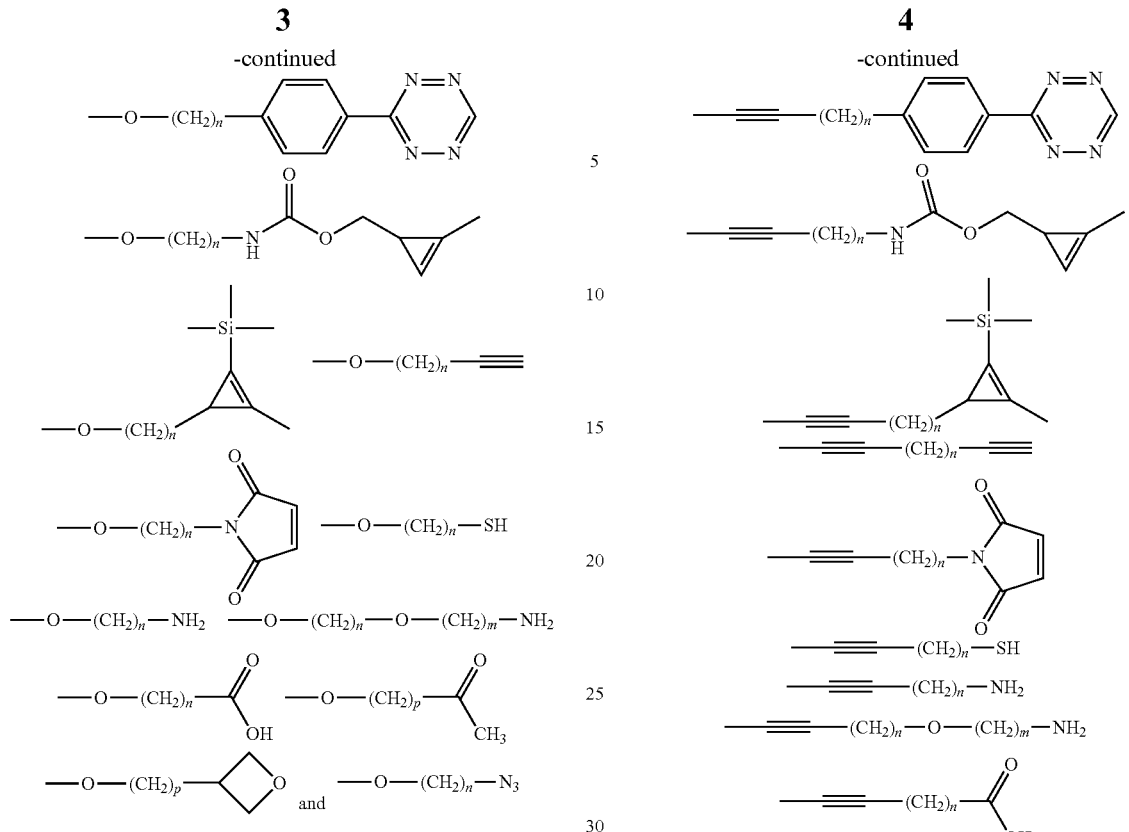

wherein n and m are independently an integer from 1 to 20 and p is an integer from 0 to 20.

Also provided herein is a compound of Formula (II):

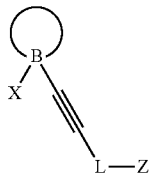

or a pharmaceutically acceptable salt thereof, wherein:

is a BODIPY ligand system;
X is a halogen;
L is absent or a linker; and
Z is selected from the group consisting of: a group reactive with a biologically active molecule and a detectable agent.

In some embodiments, the moiety (C₂)-L-Z is selected from the group consisting of:

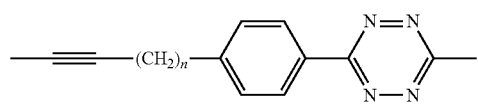

wherein n and m are each independently an integer from 1 to 20 and p is an integer from 0 to 20.

In the compounds of Formula (I) and/or (II), X can be fluorine. In some embodiments, X is $^{18}$F.

In some embodiments, the moiety Z comprises a group reactive with a biologically active molecule. In some embodiments, Z comprises a detectable agent.

Further provided herein is a method for making a compound of Formula (III):

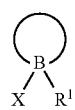

or a pharmaceutically acceptable salt thereof, wherein:

a BODIPY ligand system;
X is a halogen; and

R[1] is a substituted or unsubstituted $C_{1-20}$ alkoxy or substituted or unsubstituted $C_{1-20}$ alkynyl;

the method comprising:

reacting a compound of Formula (IV):

wherein Y is a halogen; with a compound W, wherein W comprises a Lewis Base, to prepare a compound of Formula (V):

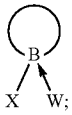

and reacting the compound of Formula (V) with HR[1] to prepare a compound of Formula (III), or a pharmaceutically acceptable salt thereof.

In some embodiments, X is fluorine. In some embodiments, X and Y are the same. For example, X and Y can both be fluorine. In some embodiments, X is $^{18}F$.

In some embodiments, R[1] is a substituted $C_{1-20}$ alkoxyl. In some embodiments, R[1] is a substituted $C_{1-20}$ alkynyl. In either case, R[1] can be substituted with a group reactive with a biologically active molecule or a detectable agent.

In some embodiments, a compound of Formula (III):

or a pharmaceutically acceptable salt thereof, can be prepared by reacting a compound of Formula (IV):

wherein Y is a halogen; with trifluoromethyl triflate to prepare a compound of Formula (V):

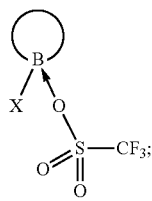

and reacting the compound of Formula (V) with HR[1] to prepare a compound of Formula (III), or a pharmaceutically acceptable salt thereof.

Also provided herein is a method for making a compound of Formula (I):

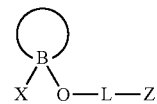

or a pharmaceutically acceptable salt thereof, wherein:

is a BODIPY ligand system;

X is a halogen;

L is absent or a linker; and

Z is selected from the group consisting of: a group reactive with a biologically active molecule and a detectable agent;

the method comprising:

reacting a compound of Formula (IV):

wherein Y is a halogen; with a compound W, wherein W comprises a Lewis Base, to prepare a compound of Formula (V):

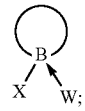

and reacting the compound of Formula (V) with HO-L-Z to prepare a compound of Formula (I), or a pharmaceutically acceptable salt thereof.

For example, a compound of Formula (I) can be prepared by reacting a compound of Formula (IV):

wherein Y is a halogen; with trifluoromethylsilyl triflate, to prepare a compound of Formula (V):

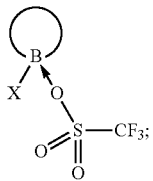

and
reacting the compound of Formula (V) with HO-L-Z to prepare a compound of Formula (I), or a pharmaceutically acceptable salt thereof.

Further provided herein is a method for making a compound of Formula (II):

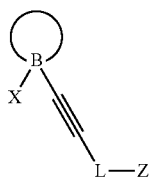

or a pharmaceutically acceptable salt thereof, wherein:

is a BODIPY ligand system;
X is a halogen;
L is absent or a linker; and
Z is selected from the group consisting of: a group reactive with a biologically active molecule and a detectable agent;
the method comprising:
reacting a compound of Formula (IV):

wherein Y is a halogen; with a compound W, wherein W comprises a Lewis Base, to prepare a compound of Formula (V):

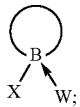

and
reacting the compound of Formula (V) with AC$_2$-L-Z, wherein A is H or a magnesium halide, to prepare a compound of Formula (I), or a pharmaceutically acceptable salt thereof.

In some embodiments, AC$_2$-L-Z is (MgBr)C$_2$-L-Z.

For example, a compound of Formula (II) can be prepared by reacting a compound of Formula (IV):

wherein Y is a halogen; with trifluoromethylsilyl triflate, to prepare a compound of Formula (V):

and
reacting the compound of Formula (V) with AC$_2$-L-Z, wherein A is H or a magnesium halide, to prepare a compound of Formula (I), or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1(a) illustrates stability of mono-alkoxy BODIPY derivatives at a concentration of 10 μM in 1×PBS ((−)Mg$^{2+}$; (−)Ca$^{2+}$; pH 7.4); FIG. 1(b) illustrates stability of mono-alkoxy BODIPY derivatives at a concentration of 1 μM in 1×PBS ((−)Mg$^{2+}$; (−)Ca$^{2+}$; pH 7.4).

FIG. 2(a) illustrates stability of mono-alkoxy BODIPY derivatives at a concentration of 10 μM in RPMI 1640 media; (−) phenol-red; (+) 10% FBS; FIG. 2(b) illustrates stability of mono-alkoxy BODIPY derivatives at a concentration of 1 μM in RPMI 1640 media; (−) phenol-red; (+) 10% FBS.

DETAILED DESCRIPTION

Definitions

Figure 1:
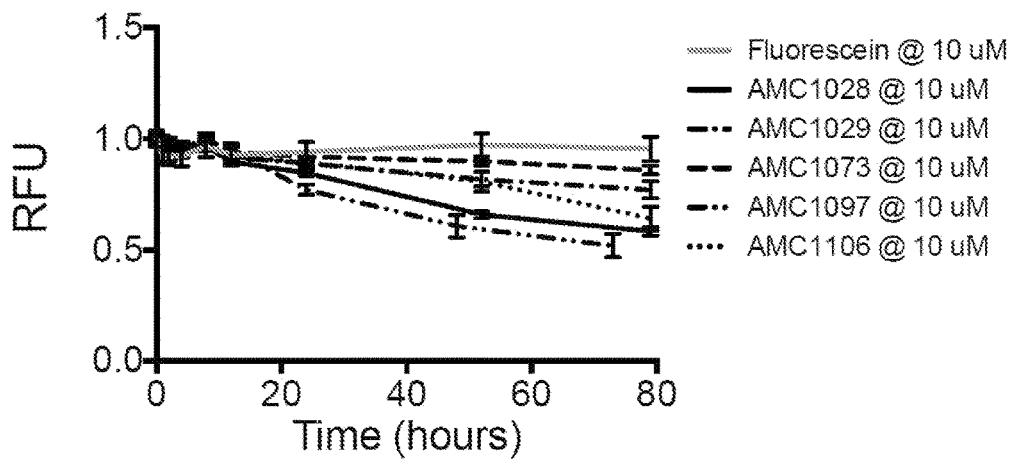
FIG. 1 is a line drawing illustrating the stability of mono-alkoxy BODIPY derivatives in aqueous buffer at room temperature over 80 hours.
Figure 1:
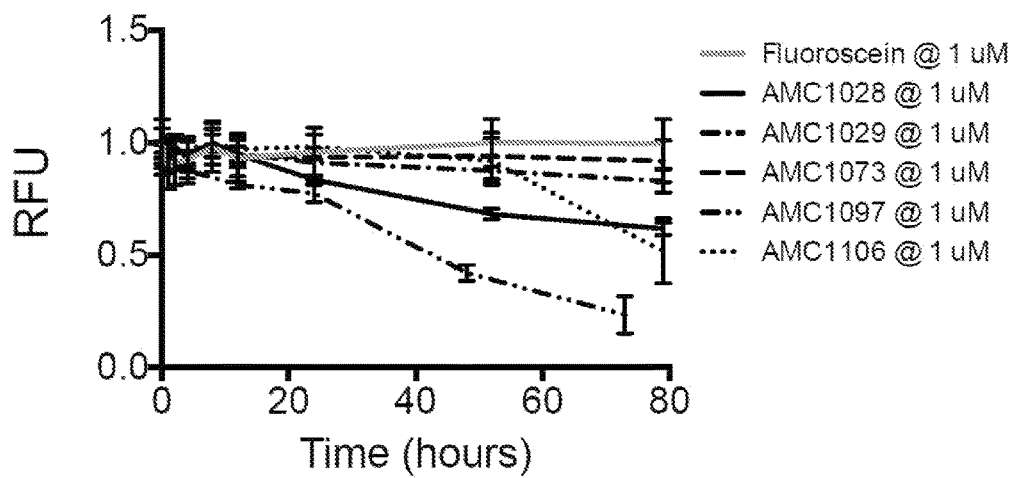

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_{1-12}$ for straight chain; $C_{3-12}$ for branched chain). The term $C_{1-12}$ includes alkyl groups containing 1 to 12 carbon atoms.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethenyl, propenyl, butenyl, pentenyl, hexenyl, heptenyl, octenyl, nonenyl, and decenyl) and branched-chain alkenyl groups. In certain embodiments, a straight chain or branched chain alkenyl group has twelve or fewer carbon atoms in its backbone (e.g., $C_{2-12}$ for straight chain; $C_{3-12}$ for branched chain). The term $C_{2-12}$ includes alkenyl groups containing 2 to 12 carbon atoms.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has twelve or fewer carbon atoms in its backbone (e.g., $C_{2-12}$ for straight chain; $C_{3-12}$ for branched chain). The term $C_{2-6}$ includes alkynyl groups containing 2 to 12 carbon atoms.

The term "alkoxy" is used in its conventional sense, and refers to alkyl groups linked to molecules via an oxygen atom. In some embodiments, an alkoxy has twelve or fewer carbon atoms in its backbone (e.g., a $C_{1-12}$ alkoxy). For example, $C_{1-10}$, $C_{1-8}$, $C_{1-6}$, $C_{1-4}$, $C_{1-3}$, or $C_{1-2}$. Non-limiting examples of an alkoxy group include methoxy, ethoxy, propoxy, butoxy, and hexoxy.

The term "cycloalkyl" includes a cyclic aliphatic group which may be saturated or unsaturated. For example, cycloalkyl groups include cyclopropyl, cyclopentyl, cyclohexyl, cycloheptyl, and cyclooctyl. In some embodiments, cycloalkyls have from 3-8 carbon atoms in their ring structure, for example, they can have 3, 4, 5 or 6 carbons in the ring structure.

In general, the term "aryl" includes groups, including 5- and 6-membered single-ring aromatic groups, such as benzene and phenyl. Furthermore, the term "aryl" includes multicyclic aryl groups, e.g., tricyclic, bicyclic, such as naphthalene and anthracene.

The term "heteroaryl" includes groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes groups, including but not limited to, 3- to 10-membered single or multiple rings having one to five heteroatoms, for example, piperazine, pyrrolidine, piperidine, or homopiperazine.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring.

Substituents include, but are not limited to, halo, $C_1$-$C_{10}$ alkyl, $C_2$-$C_{10}$ alkenyl, $C_2$-$C_{10}$ alkynyl, $C_1$-$C_{10}$alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$alkyl) wherein m is from 1 to 8, aryl, substituted aryl, substituted alkoxy, fluoroalkyl, heterocyclic radical, substituted heterocyclic radical, nitroalkyl, —$NO_2$, —CN, —$NR^9C(O)$—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR^9_2$, carbonyl, —C(O)—($C_1$-$C_{10}$ alkyl)-$CF_3$, —C(O)—$CF_3$, —C(O)$NR^9_2$, —($C_1$-$C_{10}$aryl)-($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each m is from 1 to 8, —C(O)$NR^9_2$, —C(S)$NR^9_2$, —$SO_2NR^9_2$, —$NR^9C(O)NR^9_2$, —$NR^9C(S)NR^9_2$, salts thereof, and the like. Each $R^9$ group in the preceding list independently includes, but is not limited to, H, alkyl or substituted alkyl, aryl or substituted aryl, or alkylaryl. Where substituent groups are specified by their conventional chemical Formulas, written from left to right, they equally encompass the chemically identical substituents that would result from writing the structure from right to left, for example, —$CH_2O$— is equivalent to —$OCH_2$—. In some embodiments, one or more substituents can be a group reactive with a biologically active molecule or a detectable agent.

As used herein, a "biologically active molecule" includes any molecule which can have a biological effect. Examples of biologically active molecules include therapeutic agents, small molecules, oligo- and polypeptides, oligonucleotides, coding DNA sequences, antisense DNA sequences, mRNAs, antisense RNA sequences, RNAis, and siRNAs, carbohydrates, lipids, growth factors, enzymes, transcription factors, toxins, antigenic peptides (as for vaccines), antibodies, and antibody fragments.

As used herein, chemical structures which contain one or more stereocenters depicted with dashed and bold bonds (i.e.

1) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers, enantiomers) and mixtures thereof (e.g., racemic mixtures). Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. Conventional methods for preparing salt forms are described, for example, in *Handbook of Pharmaceutical Salts: Properties, Selection, and Use*, Wiley-VCH, 2002.

The term "essentially pure" refers to chemical purity of a compound provided herein that may be substantially or essentially free of other components which normally accompany or interact with the compound prior to purification. By way of example only, a compound may be "essentially pure" when the preparation of the compound contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, an "essentially pure" compound may have a purity level of about 70%, about 75%, about 80%, about 85%, about 90%, about 95%, about 96%, about 97%, about 98%, about 99% or greater. For the purposes of this document, preparations of functionalized polymers or conjugates differing only in the length of their polymer chain are considered to be essentially pure. By way of example a preparation of a mono-functionalized compound may be "essentially pure" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating unfunctionalized and/or poly-functionalized polymers. An essentially pure compound may be obtained using chromatographic purification methods.

Compounds

Provided herein are water-soluble BODIPY derivatives. Specifically, mono-alkoxy and mono-alkyne BODIPY derivatives of Formula (I) and (II), respectively.

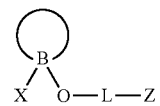

(I)

-continued

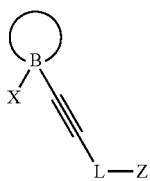
(II)

wherein:

is a BODIPY ligand system;
X is a halogen;
L is absent or a linker; and
Z is selected from the group consisting of: a group reactive with a biologically active molecule and a detectable agent.

Also provided herein is a compound of Formula (VII):

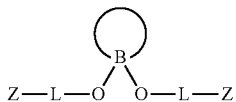

or a pharmaceutically acceptable salt thereof,
wherein:

is a BODIPY ligand system;
each L is independently absent or a linker; and
each Z is independently selected from the group consisting of: a group reactive with a biologically active molecule and a detectable agent.

A "BODIPY ligand system" as used herein refers to a substituted or unsubstituted dipyrromethene ligand complexed to boron. In some embodiments, a BODIPY ligand system includes a compound of Formula (VI):

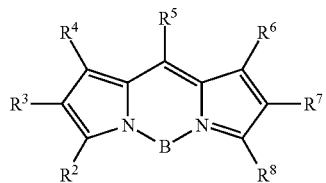

wherein:
each of $R^2$, $R^3$, $R^4$, $R^5$, $R^6$, $R^7$, and $R^8$ is independently selected from the group consisting of: H, hydroxyl, amino, halo, $CF_3$, $OCF_3$, CN, $SO_2R^9$, $(CH_2)_nOR^9$, $C(=O)NR^9R^{10}$, $SO_2NR^9R^{10}$, $NR^9SO_2R^{10}$, $COOR^9$, $NR^9C(=O)R^{10}$, $NR^9C(=O)NR^{10}$, $SO_2R^9$, $(CH_2)_nC(=O)NR^9R^{10}$, $(CH_2)_nSO_2NR^9R^{10}$, $(CH_2)_nNR^9SO_2R^{10}$, $(CH_2)_nCOOR^9$, $(CH_2)_nNR^9C(=O)R^{10}$, $(CH_2)_nNR^9C(=O)NR^{10}$, $(CH_2)_nOR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, a group reactive with a biologically active molecule, and a detectable agent; each n is an integer from 1 to 10;
each $R^9$ and $R^{10}$ is independently selected from the group consisting of: H, $CF_3$, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, a group reactive with a biologically active molecule, and a detectable agent.

In some embodiments, at least one of $R^2$, $R^3$, $R^4$, $R^5$, $R^6$, $R^7$, and $R^8$ is independently selected from the group consisting of alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, a group reactive with a biologically active molecule, and a detectable agent.

In some embodiments, $R^5$ is not H. For example, $R^5$ can be a moiety comprising Z, wherein Z is a group reactive with a biologically active molecule or a detectable agent as defined herein. The group Z can be the same or different from that conjugated to the boron center.

Non-limiting examples of a BODIPY ligand system include those found in the following BODIPY compounds:
5,5-difluoro-1,3,7,9,10-pentamethyl-5H-dipyrrolo[1,2-c:2',1'-f][1,3,2]diazaborinin-4-ium-5-uide;
4,4-Difluoro-1,3,5,7-Tetramethyl-4-Bora-3a,4a-Diaza-s-Indacene-8-Propionic Acid;
4,4-Difluoro-5,7-Dimethyl-4-Bora-3a,4a-Diaza-s-Indacene-3-Propionic Acid;
4,4-Difluoro-5,7-Dimethyl-4-Bora-3a,4a-Diaza-s-Indacene-3-Pentanoic Acid;
6-((4,4-Difluoro-5,7-Dimethyl-4-Bora-3a,4a-Diaza-s-Indacene-3-Propionyl)amino)hexanoic Acid;
4,4-Difluoro-5-Phenyl-4-Bora-3a,4a-Diaza-s-Indacene-3-Propionic Acid;
4,4-Difluoro-5,7-Diphenyl-4-Bora-3a,4a-Diaza-s-Indacene-3-Propionic Acid;
6-((4,4-Difluoro-1,3-Dimethyl-5-(4-Methoxyphenyl)-4-Bora-3a,4a-Diaza-s-Indacene-2-Propionyl)amino) hexanoic Acid;
4,4-Difluoro-5-(2-Thienyl)-4-Bora-3a,4a-Diaza-s-Indacene-3-Propionic Acid;
4,4-Difluoro-5-Styryl-4-Bora-3a,4a-Diaza-s-Indacene-3-Propionic Acid;
4,4-Difluoro-5-(2-Pyrrolyl)-4-Bora-3a,4a-Diaza-s-Indacene-3-Propionic Acid;
4,4-Difluoro-5-(4-Phenyl-1,3-Butadienyl)-4-Bora-3a,4a-Diaza-s-Indacene-3-Propionic Acid;
6-(((4-(4,4-Difluoro-5-(2-Thienyl)-4-Bora-3a,4a-Diaza-s-Indacene-3-yl)phenoxy)acetyl)amino)hexanoic Acid;
6-(((4,4-Difluoro-5-(2-Thienyl)-4-Bora-3a,4a-Diaza-s-Indacene-3-yl)styryloxy)acetyl)aminohexanoic Acid;
6-(((4,4-Difluoro-5-(2-Pyrrolyl)-4-Bora-3a,4a-Diaza-s-Indacene-3-yl)Styryloxy)Acetyl)Aminohexanoic Acid;
5-butyl-4,4-difluoro-4-bora-3a,4a-diaza-s-indacene-3-nonanoic acid;
5-decyl-4,4-difluoro-4-bora-3a,4a-diaza-s-indacene-3-propionic acid;

4,4-difluoro-5,7-dimethyl-4-bora-3a,4a-diaza-s-indacene-3-dodecanoic acid;
4,4-difluoro-5,7-dimethyl-4-bora-3a,4a-diaza-s-indacene-3-hexadecanoic acid;
4,4-difluoro-5,7-dimethyl-4-bora-3a,4a-diaza-s-indacene-3-pentanoic acid;
4,4-difluoro-5,7-dimethyl-4-bora-3a,4a-diaza-s-indacene-3-undecanoic acid;
4,4-difluoro-5,7-diphenyl-4-bora-3a,4a-diaza-s-indacene-3-dodecanoic acid;
4,4-difluoro-5-methyl-4-bora-3a,4a-diaza-s-indacene-3-dodecanoic acid;
4,4-difluoro-5-octyl-4-bora-3a,4a-diaza-s-indacene-3-pentanoic acid;
4,4-difluoro-5-(4-phenyl-1,3-butadienyl)-4-bora-3a,4a-diaza-s-indacene-3-pentanoic acid;
4,4-difluoro-5-(4-phenyl-1,3-butadienyl)-4-bora-3a,4a-diaza-s-indacene-3-undecanoic acid;
4,4-difluoro-5-(2-thienyl)-4-bora-3a,4a-diaza-s-indacene-3-dodecanoic acid;
2-(4,4-difluoro-5,7-dimethyl-4-bora-3a,4a-diaza-s-indacene-3-dodecanoyl)-1-hexadecanoyl-sn-glycero-3-phosphocholine;
2-(4,4-difluoro-5,7-dimethyl-4-bora-3a,4a-diaza-s-indacene-3-pentanoyl)-1-hexadecanoyl-sn-glycero-3-phosphocholine;
2-(4,4-difluoro-5-methyl-4-bora-3a,4a-diaza-s-indacene-3-dodecanoyl)-1-hexadecanoyl-sn-glycero-3-phosphocholine;
2-(4,4-difluoro-5-octyl-4-bora-3a,4a-diaza-s-indacene-3-pentanoyl)-1-hexadecanoyl-sn-glycero-3-phosphocholine;
2-(4,4-difluoro-5-(4-phenyl-1,3-butadienyl)-4-bora-3a,4a-diaza-s-indacene-3-pentanoyl)-1-hexadecanoyl-sn-glycero-3-phosphocholine;
2-(4,4-difluoro-5,7-dimethyl-4-bora-3a,4a-diaza-s-indacene-3-pentanoyl)-1-hexadecanoyl-sn-glycero-3-phosphate;
N-(4,4-difluoro-5,7-dimethyl-4-bora-3a,4a-diaza-s-indacene-3-propionyl)-1,2-dihexadecanoyl-sn-glycero-3-phosphoethanolamine;
N-(4,4-difluoro-5,7-dimethyl-4-bora-3a,4a-diaza-s-indacene-3-propionyl)-1,2-dihexanoyl-sn-glycero-3-phosphoethanolamine
cholesteryl 4,4-difluoro-5,7-dimethyl-4-bora-3a,4a-diaza-s-indacene-3-dodecanoate;
cholesteryl 4,4-difluoro-5-(4-methoxyphenyl)-4-bora-3a,4a-diaza-s-indacene-3-undecanoate;
cholesteryl 4,4-difluoro-5-(2-pyrrolyl)-4-bora-3a,4a-diaza-s-indacene-3-undecanoate;
4,4-difluoro-1,3,5,7,8-pentamethyl-4-bora-3a,4a-diaza-s-indacene;
4,4-difluoro-1,3,5,7-tetramethyl-4-bora-3a,4a-diaza-s-indacene;
N-(4,4-Difluoro-5,7-Dimethyl-4-Bora-3a,4a-Diaza-s-Indacene-3-yl)Methyl)Iodoacetamide;
N-(4,4-Difluoro-1,3,5,7-Tetramethyl-4-Bora-3a,4a-Diaza-s-Indacene-2-yl)Iodoacetamide;
8-Bromomethyl-4,4-Difluoro-1,3,5,7-Tetramethyl-4-Bora-3a,4a-Diaza-s-Indacene or pharmaceutically acceptable salts and/or ester derivatives thereof. In some embodiments, a pharmaceutically acceptable salt includes sodium, diammonium, and triethylammonium. In some embodiments, a pharmaceutically acceptable ester derivative includes succinimidyl ester and sulfosuccinimidyl ester derivatives.

Also contemplated herein are the BODIPY ligand systems found on the BODIPY compounds described in Ulrich, G. et al., *Angew. Chem. Int. Ed* 2008, 47: 1184-1201; Ziessel, R. et al., *New J. Chem.* 2007, 31: 496-501; and Loudet, A. and Burgess, K., *Chem. Rev.* 2007, 107: 4891-4932, all of which are incorporated by reference in their entirety herein.

X is a halogen. For example, X is selected from the group consisting of F, Cl, Br, and I. In some embodiments, X is F. In some embodiments, X is a radioactive halogen (e.g., $^{18}$F.).

The term "linker" as used herein refers to a group of atoms, (e.g., 1-500 atoms, 1-250 atoms, 1-100 atoms, and 1-50 atoms) and can be comprised of the atoms or groups of atoms such as, but not limited to, hydrogen and carbon, e.g., methylene (—CH$_2$—), amino, amido, alkylamino, oxygen, polyethylene glycol (PEG), peptoid, sulfur, sulfoxide, sulfonyl, carbonyl, and imine. The linker can also comprise part of a saturated, unsaturated or aromatic ring, including polycyclic and heteroaromatic rings wherein the heteroaromatic ring is an aryl group containing from one to four heteroatoms, N, O or S.

Specific examples include, but are not limited to, saturated $C_{1-20}$ alkanes, $C_{1-20}$ alkyl ethers, $C_{1-20}$ alkyl diamines, and $C_{1-20}$ alkyl chains having one or more peptide bonds.

The linker must not interfere with the imaging methods or with the bioorthogonal conjugation reactions described herein.

In some embodiments, L is absent. In some embodiments, L is —(CH$_2$)$_n$—, wherein n is an integer from 1 to 20 (e.g., 1 to 10, 1 to 5, and 1 to 3). In some embodiments, L is —(CH$_2$)$_n$—O—(CH$_2$)$_m$—, wherein n and m are independently an integer from 1 to 20 (e.g., 1 to 10, 1 to 5, and 1 to 3). In some embodiments, L is —(OCH$_2$CH$_2$)$_n$—, wherein n is an integer from 1 to 20 (e.g., 1 to 10, 1 to 5, and 1 to 3).

The term "group reactive with a biologically active molecule" refers to a functional group that can be covalently bound to a functional group of a biologically active molecule. Non-limiting examples of a group reactive with a biologically active molecule include: hydroxyl, amine, amine glycol, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide, tetrazine, and cyclopropene.

In some embodiments, the group reactive with a biologically active molecule comprises moieties which are capable of undergoing bio-orthogonal reactions. Bio-orthogonal reactions comprise a class of chemoselective couplings highly suited for applications in chemical biology (Devaraj, N. K.; Weissleder, R. *Acc. Chem. Res.* 2011, 44, 816-827). These reactions engage very selective binding partners, are biocompatible, and can be performed at room-temperature with reasonable reaction kinetics. They have been shown to hold usability in a diverse array of imaging contexts such as in cellular nanoparticle labeling (Haun, J. B.; Devaraj, N. K.; Hilderbrand, S. A.; Lee, H.; Weissleder, R. 2010, 1-6) and introduction of $^{18}$F onto small molecule inhibitors for PET (Reiner, T.; Keliher, E. J.; Earley, S.; Marinelli, B.; Weissleder, R. *Angew. Chem. Int. Ed. Engl.* 2011, 50, 1922-1925). One of the most promising bio-orthogonal reactions for widespread use in chemical biology is the [4+2]cycloaddition between a 1,2,4,5-tetrazine and a trans-cyclooctene (TCO) or cyclopropene (Yang, J.; Šečkutė, J.; Cole, C. M.; Devaraj, N. K. *Angew. Chem. Int. Ed.* 2012, n/a-n/a). Examples of bioorthogonal groups can be found, for example, in Sletten, E M and Bertozzi, C R, *Angew. Chem. Int. Ed.* 2009 48: 6974-6998.

In some embodiments, the moiety —O-L-Z is selected from the group consisting of:

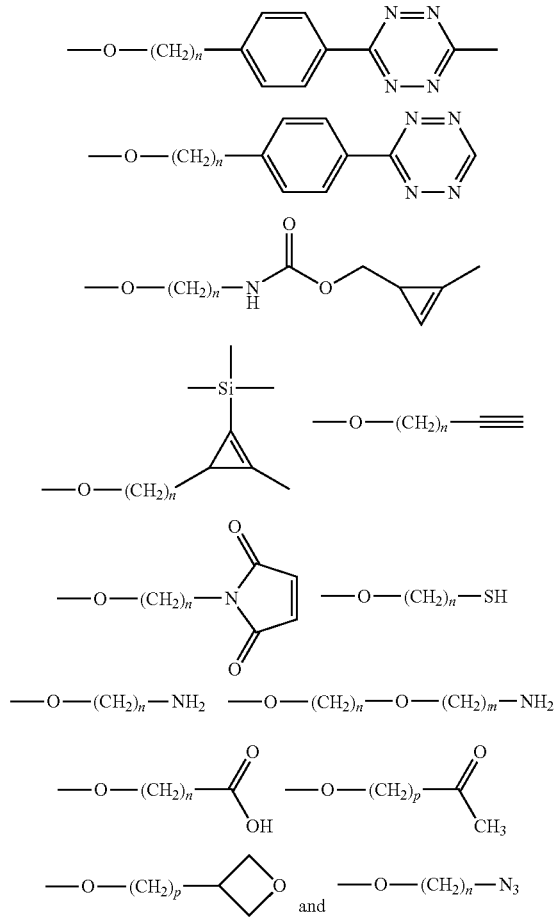

wherein n and m are independently integers from 1 to 20 (e.g., 1, 2, 3, 4, 5, 6, 7, 8, 9, 10, 11, 12, 13, 14, 15, 16, 17, 18, 19, or 20); and p is an integer from 0 to 20 (e.g., 0, 1, 2, 3, 4, 5, 6, 7, 8, 9, 10, 11, 12, 13, 14, 15, 16, 17, 18, 19, or 20). In some embodiments, n and m are independently integers from 1 to 10 (e.g., 1 to 8, 1 to 6, 1 to 5, and 1 to 3) and p is an integer from 0 to 10 (e.g., 0 to 8, 0 to 6, 0 to 5, and 0 to 3). For example, n and m can independently be integers from 1 to 3 and p can be an integer from 0 to 3. In some embodiments, the moiety —O-L-Z is selected from the group consisting of:

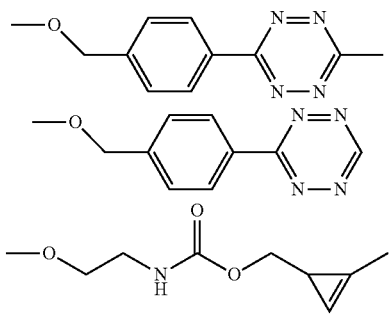

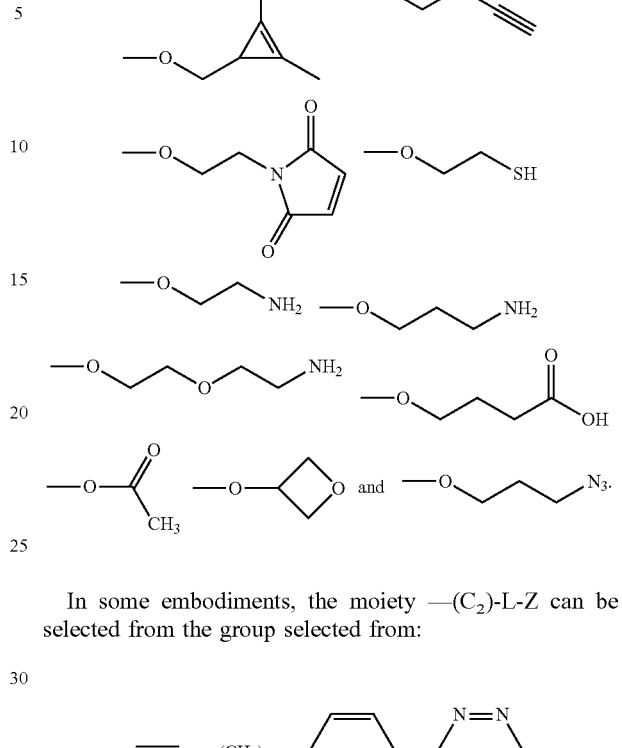

In some embodiments, the moiety —(C$_2$)-L-Z can be selected from the group selected from:

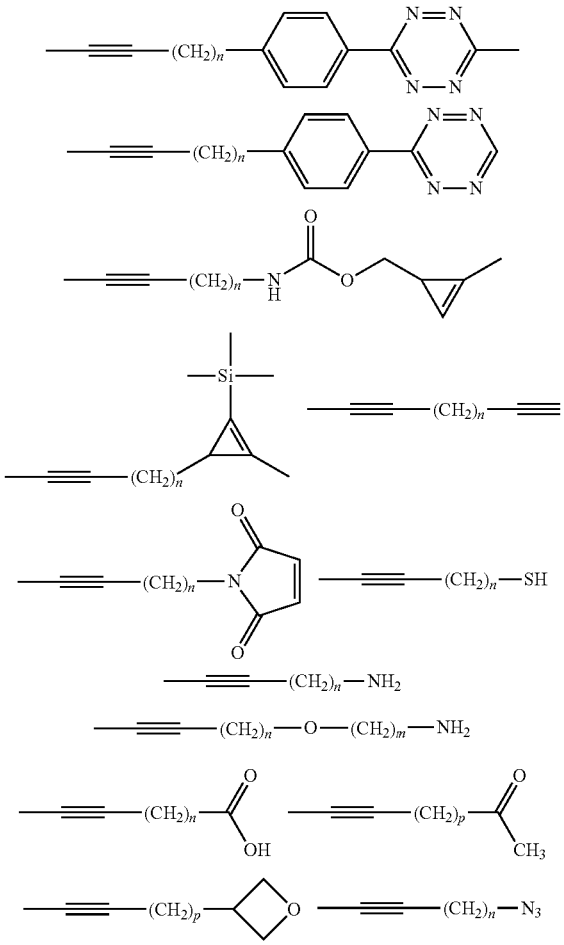

-continued

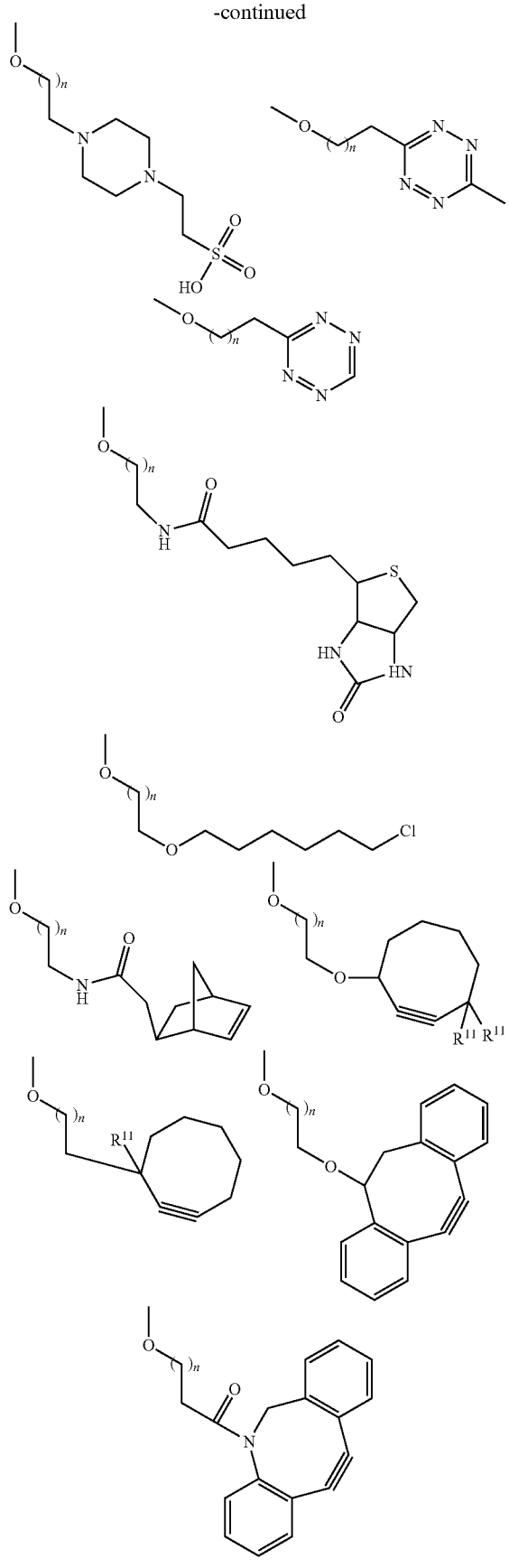

wherein n and m are independently integers from 1 to 20 (e.g., 1, 2, 3, 4, 5, 6, 7, 8, 9, 10, 11, 12, 13, 14, 15, 16, 17, 18, 19, or 20); and p is an integer from 0 to 20 (e.g., 0, 1, 2, 3, 4, 5, 6, 7, 8, 9, 10, 11, 12, 13, 14, 15, 16, 17, 18, 19, or 20). In some embodiments, n and m are independently integers from 1 to 10 (e.g., 1 to 8, 1 to 6, 1 to 5, and 1 to 3) and p is an integer from 0 to 10 (e.g., 0 to 8, 0 to 6, 0 to 5, and 0 to 3). For example, n and m can independently be integers from 1 to 3 and p can be an integer from 0 to 3. In some embodiments, the moiety —O-L-Z is selected from the group consisting of:

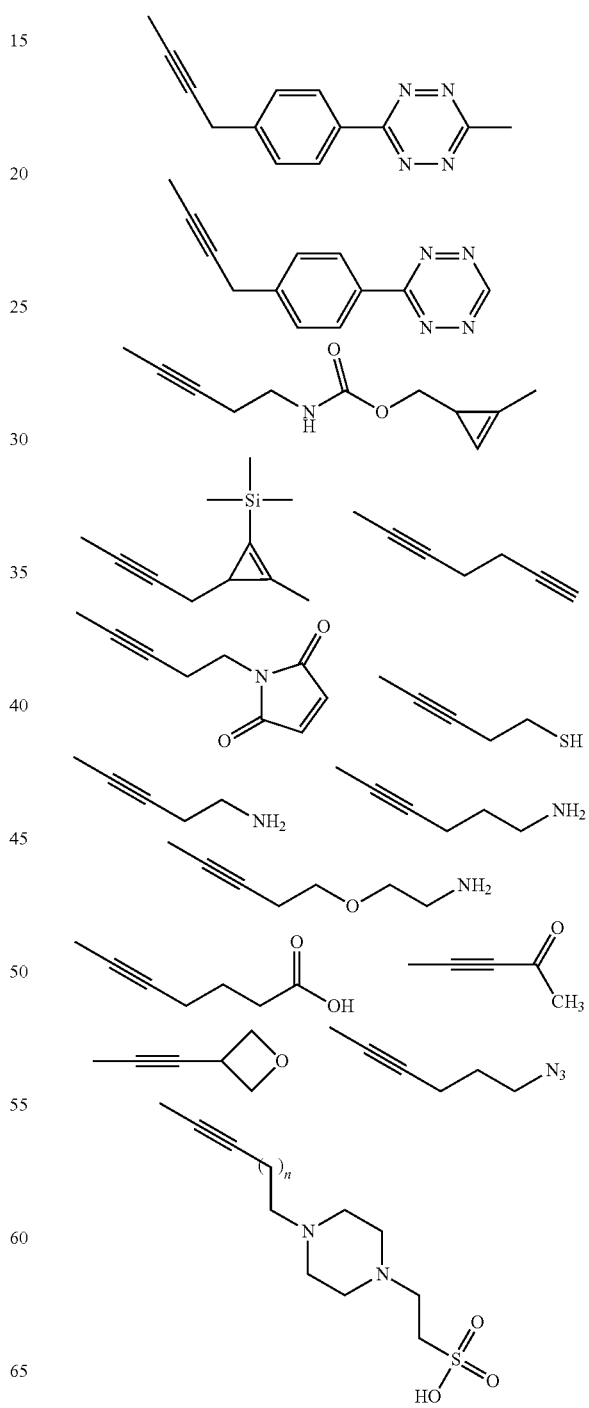

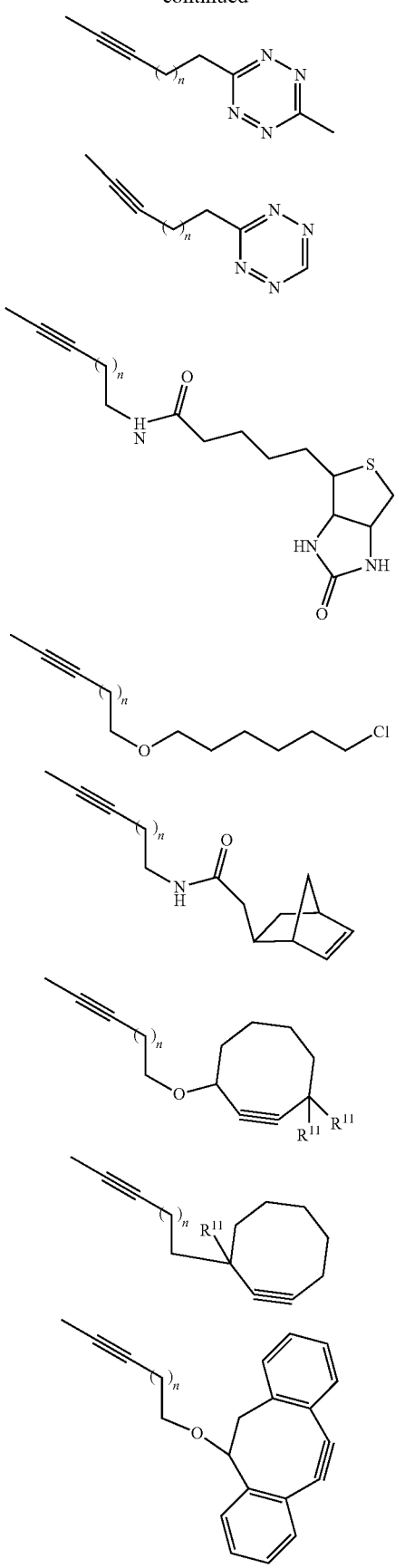

Examples of detectable agents include various organic small molecules, inorganic compounds, nanoparticles, enzymes or enzyme substrates, fluorescent materials, luminescent materials, bioluminescent materials, chemiluminescent materials, magnetic materials, radioactive materials, and contrast agents. In some embodiments, the detectable agent is a radioactive material or a fluorescent material.

Examples of suitable enzymes include horseradish peroxidase, alkaline phosphatase, beta-galactosidase, or acetylcholinesterase.

Examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl)aminohexanoic acid, succinimidyl ester (BODIPY® 650/665-X), 7-N,N-diethylaminocoumarin, sulforhodamine 101 acid chloride (Texas Red), VIVOTAG 680 (an amine-reactive near-infra-red fluorochrome, from VisEn Medical), umbelliferone, fluorescein, fluorescein isothiocyanate, rhodamine, dichlorotriazinylamine fluorescein, dansyl chloride or phycoerythrin.

An example of a luminescent material includes luminol.

Examples of bioluminescent materials include luciferase, luciferin, and aequorin.

Examples of suitable radioactive materials include $^{11}C$, $^{13}N$, $^{15}O$, $^{18}F$, $^{67}Ga$, $^{81m}Kr$, $^{82}Rb$, $^{86}Y$, $^{89}Zr$, $^{111}In$, $^{123}I$, $^{124}I$, $^{133}Xe$, $^{201}Tl$, $^{125}I$, $^{35}S$, $^{14}C$, or $^{3}H$, $^{64}Cu$, $^{99m}Tc$ (e.g., as pertechnetate (technetate(VII), $TcO_4^-$) either directly or indirectly, $^{123}I$, or other radioisotope detectable by direct counting of radioemmission or by scintillation counting.

In some embodiments, the radioactive material is complexed by a suitable ligand modality. Such ligands are well known in the art. For example, a ligand can include DTPA, DTPE, DOTA, NOTA, DO3A, DDPE, and DOTAGA. In some embodiments, a radioisotope is conjugated to the compound directly or indirectly via a linker (e.g., an alkyl or ether linker). In addition, contrast agents, e.g., contrast agents for MRI or NMR, for X-ray CT, Raman imaging, optical coherence tomography, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates is (e.g., Mn-DPDP), barium sulfate, iodinated contrast media (iohexol), microbubbles, or perfluorocarbons can also be used. In some embodiments, the detectable agent is an MRI contrast agent such as gadodiamide (OMNISCAN®), gadobenate (MULTIHANCE®), gadopentetate (MAGNEVIST®), gadoteridol (PROHANCE®), gadofosveset (ABLAVAR®, formerly VASOVIST®), gadoversetamide (OPTIMARK®), gadoxetate (EOVIST®), and gadobutrol (GADAVIST®).

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))

When the compounds are enzymatically labeled with, for example, horseradish peroxidase, alkaline phosphatase, or luciferase, the enzymatic label is detected by determination of conversion of an appropriate substrate to product.

Non-limiting examples of a compound of Formula (I) include:

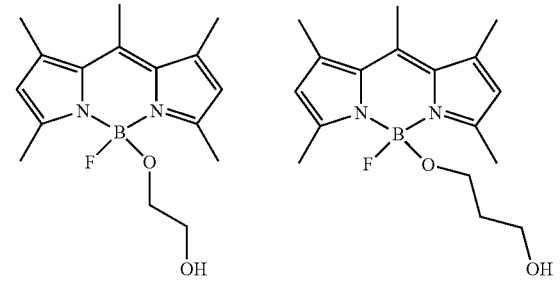

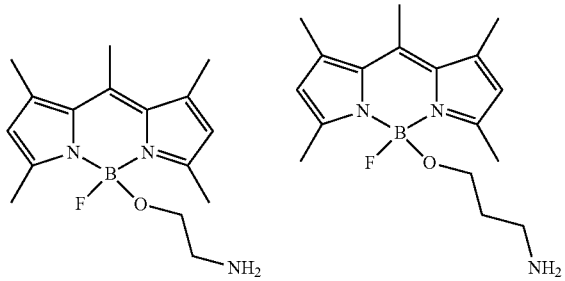

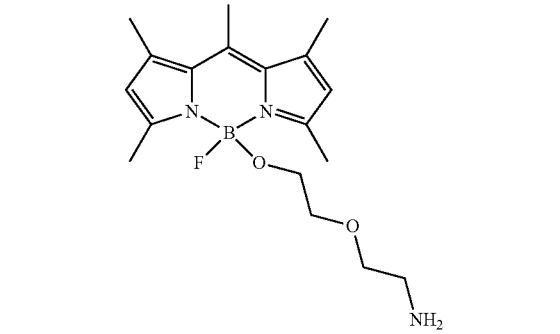

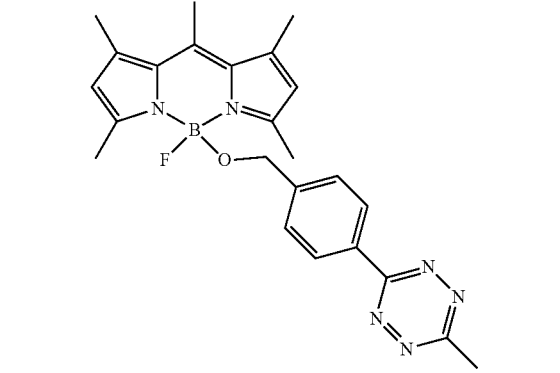

-continued

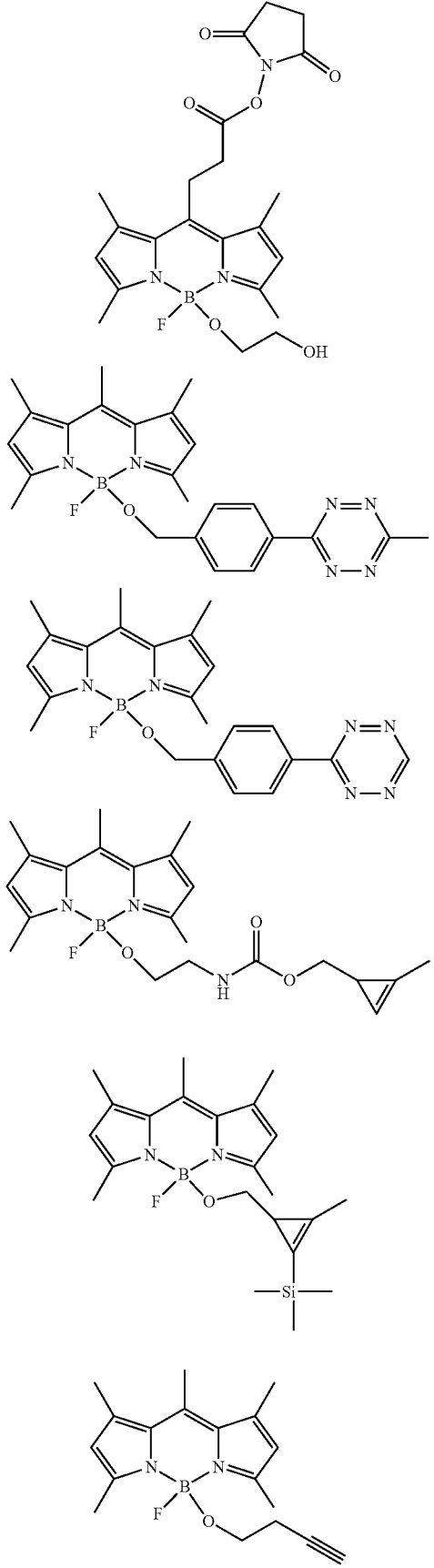

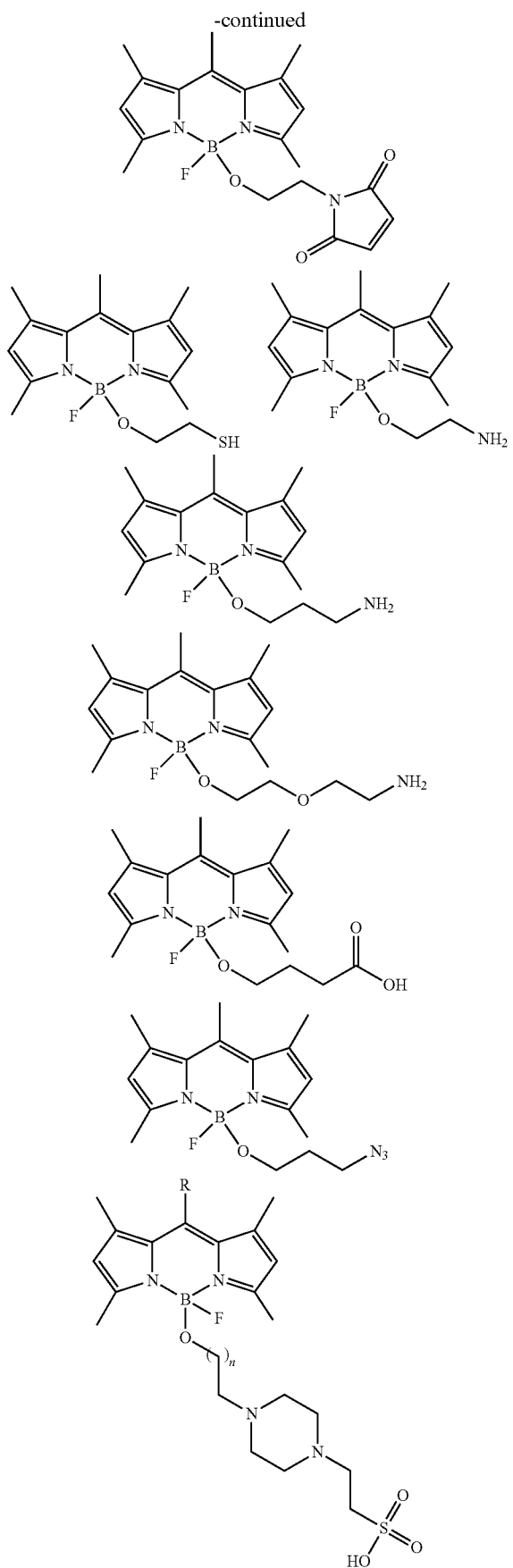
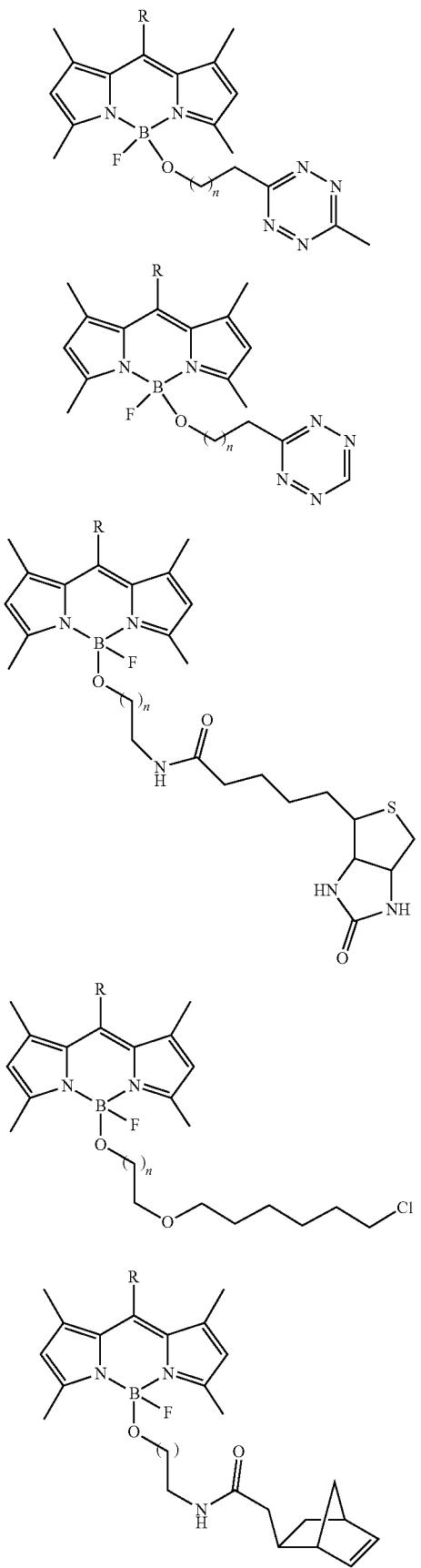

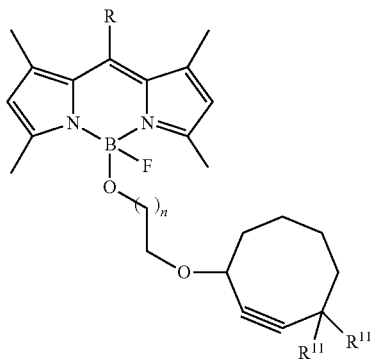
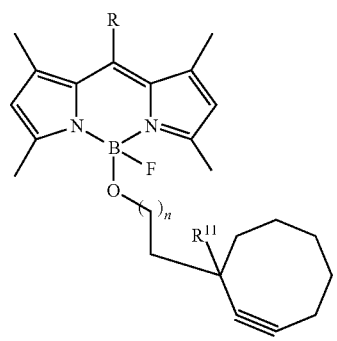
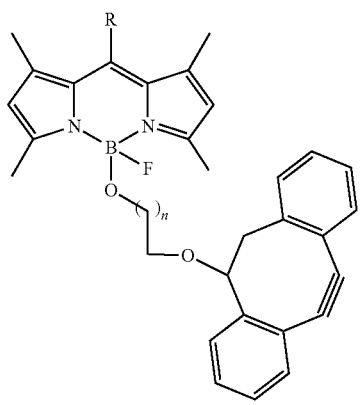
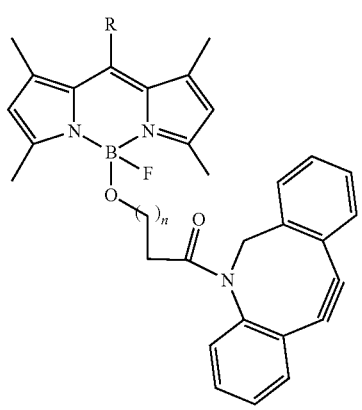
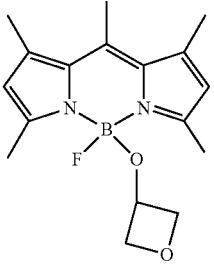
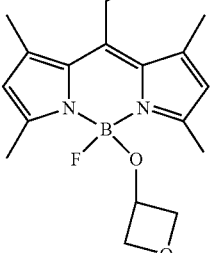
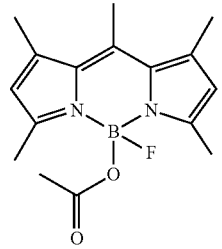
wherein each n is independently an integer from 1 to 20; R is any reasonable moiety that does not interfere with the O-L-Z moiety, for example, $R^5$ as defined above. Each $R^{11}$ is independently selected from H and F (e.g., $^{18}F$).
Non-limiting examples of a compound of Formula (II) include:
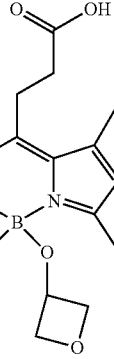

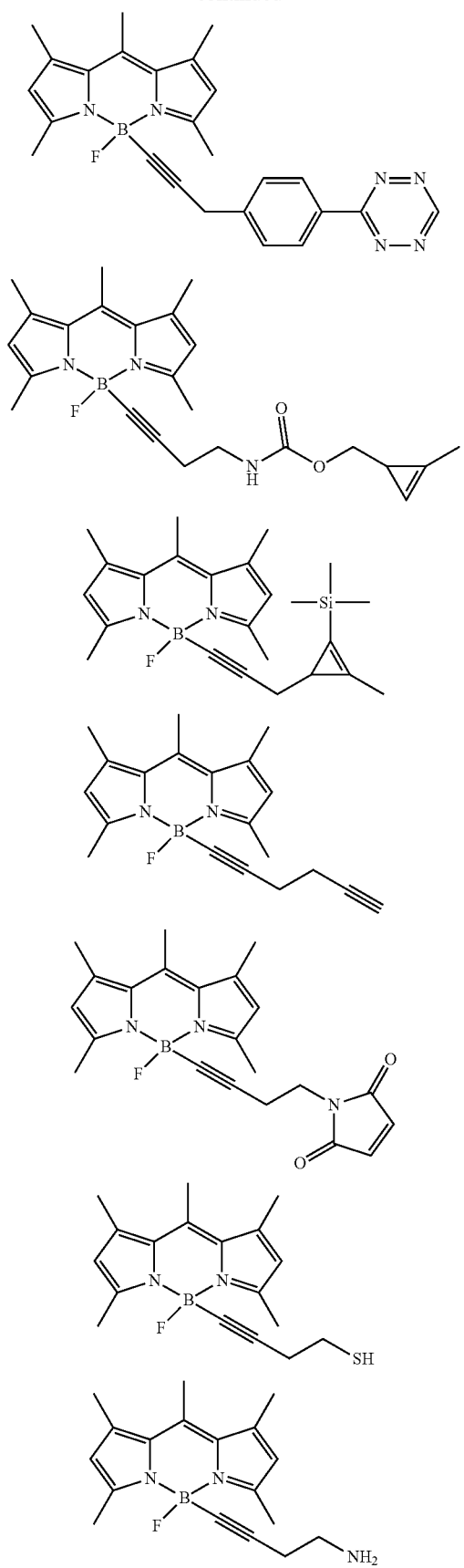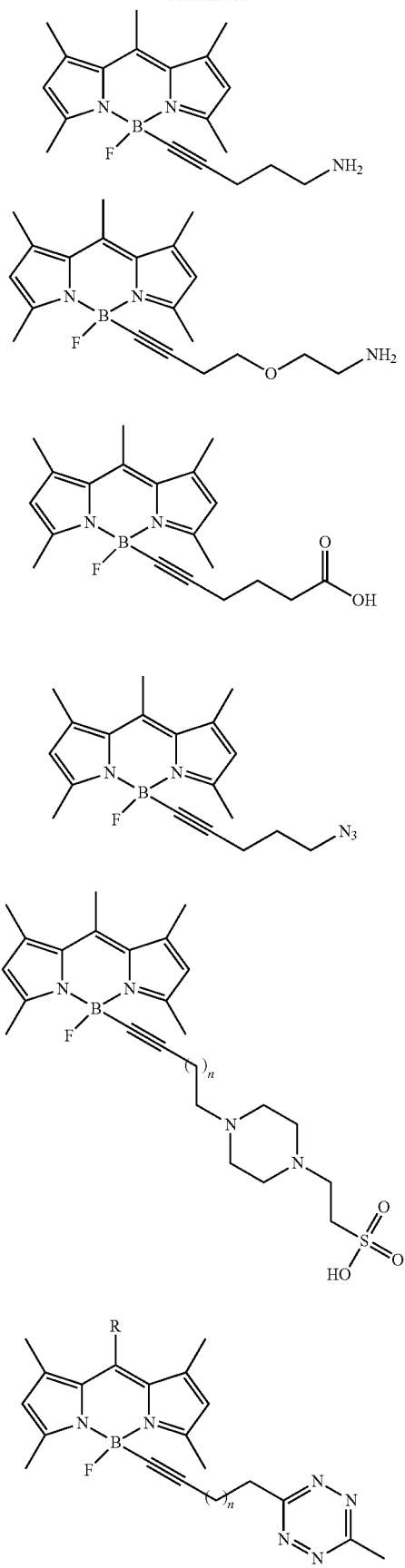

31
-continued
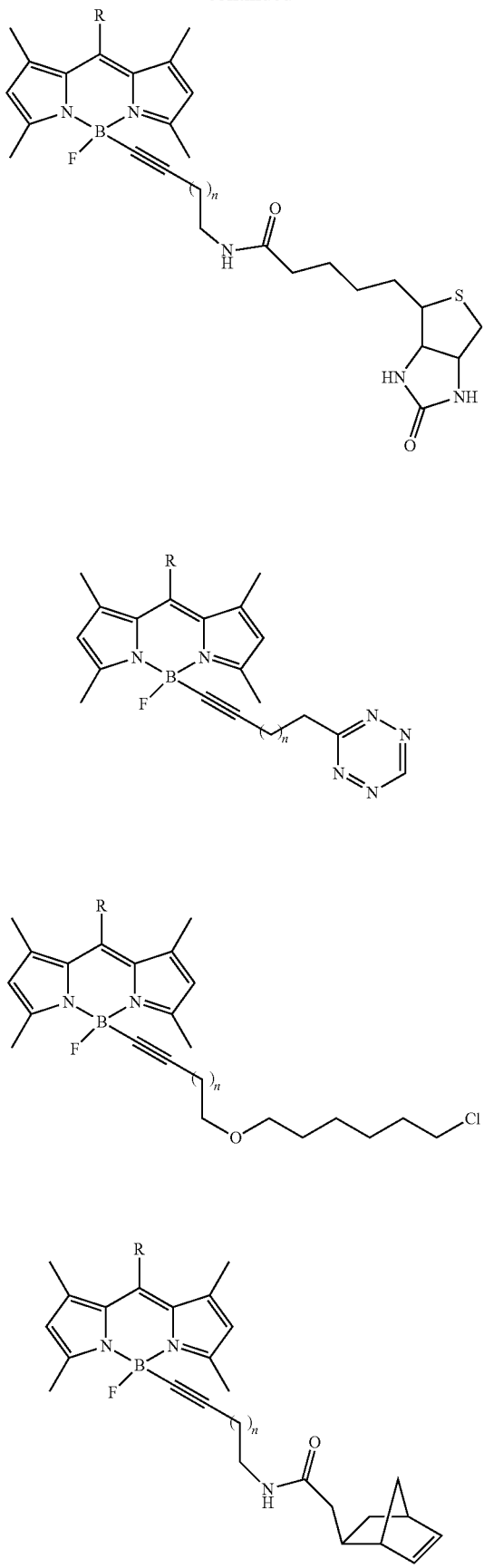
32
-continued
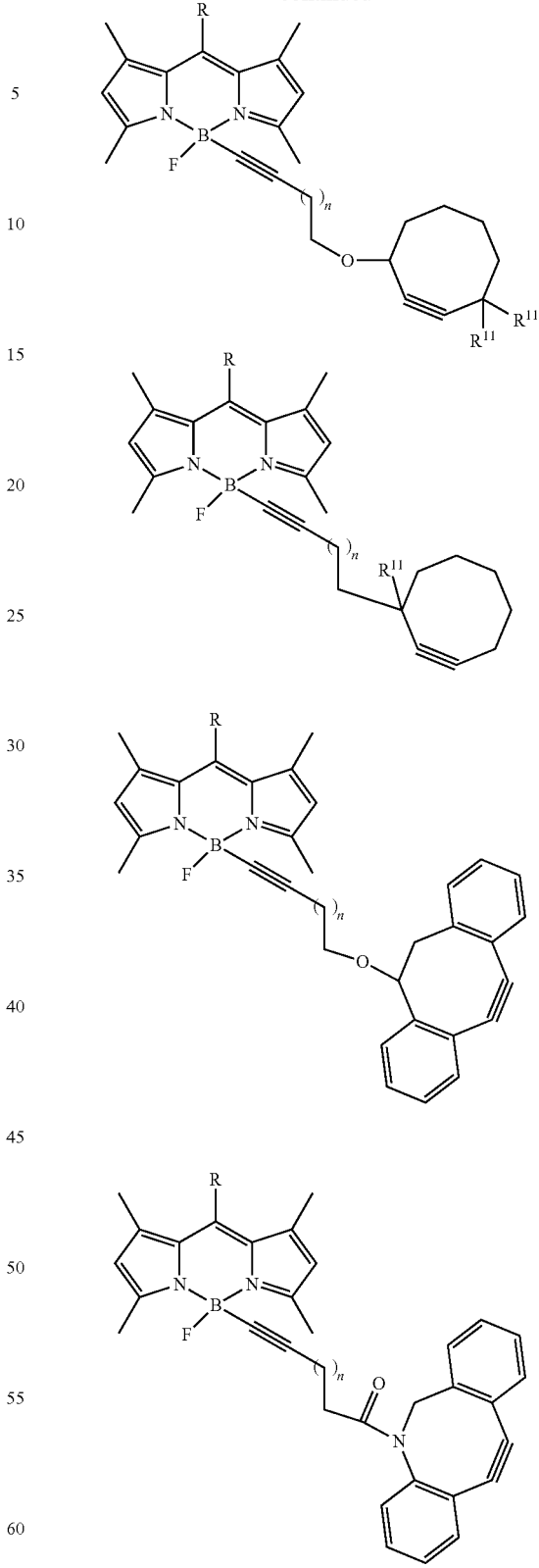
wherein each n is independently an integer from 1 to 20; R is any reasonable moiety that does not interfere with the O-L-Z moiety, for example, $R^5$ as defined above. Each $R^{11}$ is independently selected from H and F (e.g., $^{18}F$).

Non-limiting examples of a compound of Formula (VII) include:

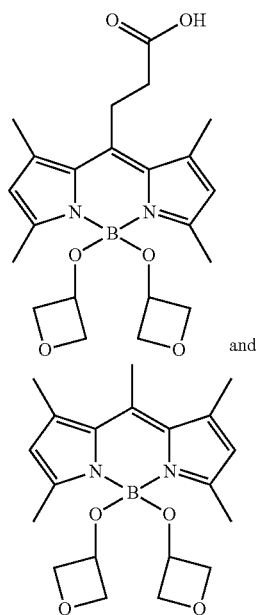

and or a pharmaceutically acceptable salt thereof.

Synthetic Methods

Provided herein are methods for preparing water-soluble mono-alkoxy and mono-alkyne BODIPY derivatives.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1st Ed., Oxford University Press, 2000; *March's Advanced Organic Chemistry: Reactions, Mechanisms, and Structure*, 5th Ed., Wiley-Interscience Publication, 2001; and Peturssion, S. et al., "*Protecting Groups in Carbohydrate Chemistry,*" *J. Chem. Educ.*, 74(11), 1297 (1997) (each of which is incorporated herein by reference in its entirety).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

See, for example, Hendricks, J. A.; Keliher, E. J.; Wan, D.; Hilderbrand, S. A.; Weissleder, R.; Mazitschek, R. *Angew. Chem. Int. Ed. Engl.* 2012, 51, 4603-4606.

Provided herein is a method for preparing a compound of Formula (III):

or a pharmaceutically acceptable salt thereof, wherein:

is a BODIPY ligand system;
X is a halogen; and
$R^1$ is a substituted or unsubstituted $C_{1-20}$ alkoxy or a substituted or unsubstituted $C_{1-20}$ alkynyl.

A compound of Formula (III) can be prepared as shown in Scheme I. For example, a BODIPY compound of Formula (IV) can be reacted with a compound is comprising a Lewis Base (W) to give a compound of Formula (V). The compound of Formula (V) can then be reacted with an alcohol or alkyne (HR$^1$) to result in the Formulation of a compound of Formula (III).

Scheme 1

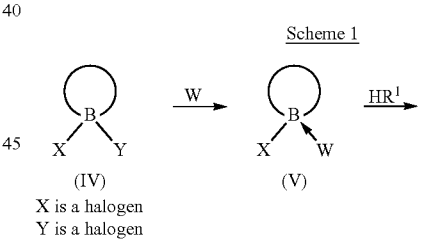

(IV)
X is a halogen
Y is a halogen (V)

(III)

$R^1$ is a substituted or
unsubstituted $C_{1-20}$ alkoxyl
or a substituted or unsubstituted
$C_{1-20}$ alkynyl A. Compounds of Formula (IV)

A compound of Formula (IV) can be any BODIPY compound. As used herein, "BODIPY" refers to fluorescent dyes composed of dipyrromethene complexed with a disubstituted boron atom, e.g., a BX$_2$ unit such as BF$_2$. Accordingly, in some embodiments, X and Y can be selected from the group consisting of: F, Cl, Br, and I. X and Y can be the same or different. For example, X and Y can both be F. In some embodiments, one or more of X or Y is a radioactive halogen (e.g., $^{18}$F.). As would be understood by one of skill in the art, many BODIPY compounds are known and may be used in the compounds and methods described herein.

In some embodiments, a compound of Formula (IV) is a compound of Formula (VII):

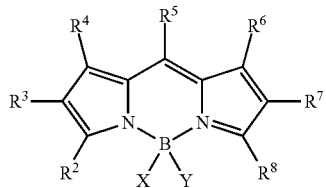

wherein:
each of $R^2$, $R^3$, $R^4$, $R^5$, $R^6$, $R^7$, and R is independently selected from the group consisting of: H, hydroxyl, amino, halo, $CF_3$, $OCF_3$, CN, $SO_2R^9$, $(CH_2)_nOR^9$, $C(=O)NR^9R^{10}$, $SO_2NR^9R^{10}$, $NR^9SO_2R^{10}$, $COOR^9$, $NR^9C(=O)R^{10}$, $NR^9C(=O)NR^{10}$, $SO_2R^9$, $(CH_2)_nC(=O)NR^9R^{10}$, $(CH_2)_nSO_2NR^9R^9$, $(CH_2)_nNR^9SO_2R^{10}$, $(CH_2)_nCOOR^9$, $(CH_2)_nNR^9C(=O)R^{10}$, $(CH_2)_nNR^9C(=O)NR^{10}$, $(CH_2)_nOR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, a group reactive with a biologically active molecule, and a detectable agent;
each n is an integer from 1 to 10;
each $R^9$ and $R^{10}$ is independently selected from the group consisting of: H, $CF_3$, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, a group reactive with a biologically active molecule, and a detectable agent.

In some embodiments, at least one of $R^2$, $R^3$, $R^4$, $R^5$, $R^6$, $R^7$, and $R^8$ is independently selected from the group consisting of alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, a group reactive with a biologically active molecule, and a detectable agent.

In some embodiments, $R^5$ is not H. For example, $R^5$ can be a moiety comprising Z, wherein Z is a group reactive with a biologically active molecule or a detectable agent as defined herein.

In some embodiments, X and Y can be selected from the group consisting of: F, Cl, Br, and I. X and Y can be the same or different. For example, X and Y can both be F.

In some embodiments, one or more of X or Y is a radioactive halogen (e.g., $^{18}$F.).

Non-limiting examples of a compound of Formula (IV) include:
5,5-difluoro-1,3,7,9,10-pentamethyl-5H-dipyrrolo[1,2-c:2',1'-f][1,3,2]diazaborinin-4-ium-5-uide;
4,4-Difluoro-1,3,5,7-Tetramethyl-4-Bora-3a,4a-Diaza-s-Indacene-8-Propionic Acid;
4,4-Difluoro-5,7-Dimethyl-4-Bora-3a,4a-Diaza-s-Indacene-3-Propionic Acid;
4,4-Difluoro-5,7-Dimethyl-4-Bora-3a,4a-Diaza-s-Indacene-3-Pentanoic Acid;
6-((4,4-Difluoro-5,7-Dimethyl-4-Bora-3a,4a-Diaza-s-Indacene-3-Propionyl)amino)hexanoic Acid;
4,4-Difluoro-5-Phenyl-4-Bora-3a,4a-Diaza-s-Indacene-3-Propionic Acid;
4,4-difluoro-5,7-Diphenyl-4-Bora-3a,4a-Diaza-s-Indacene-3-Propionic Acid;
6-((4,4-Difluoro-1,3-Dimethyl-5-(4-Methoxyphenyl)-4-Bora-3a,4a-Diaza-s-Indacene-2-Propionyl)amino)hexanoic Acid;
4,4-Difluoro-5-(2-Thienyl)-4-Bora-3a,4a-Diaza-s-Indacene-3-Propionic Acid;
4,4-Difluoro-5-Styryl-4-Bora-3a,4a-Diaza-s-Indacene-3-Propionic Acid;
4,4-Difluoro-5-(2-Pyrrolyl)-4-Bora-3a,4a-Diaza-s-Indacene-3-Propionic Acid;
4,4-Difluoro-5-(4-Phenyl-1,3-Butadienyl)-4-Bora-3a,4a-Diaza-s-Indacene-3-Propionic Acid;
6-(((4-(4,4-Difluoro-5-(2-Thienyl)-4-Bora-3a,4a-Diaza-s-Indacene-3-yl)phenoxy)acetyl)amino)hexanoic Acid;
6-(((4,4-Difluoro-5-(2-Thienyl)-4-Bora-3a,4a-Diaza-s-Indacene-3-yl)styryloxy)acetyl)amino)hexanoic Acid;
6-(((4,4-Difluoro-5-(2-Pyrrolyl)-4-Bora-3a,4a-Diaza-s-Indacene-3-yl)Styryloxy)Acetyl)Aminohexanoic Acid;
5-butyl-4,4-difluoro-4-bora-3a,4a-diaza-s-indacene-3-nonanoic acid;
5-decyl-4,4-difluoro-4-bora-3a,4a-diaza-s-indacene-3-propionic acid;
4,4-difluoro-5,7-dimethyl-4-bora-3a,4a-diaza-s-indacene-3-dodecanoic acid;
4,4-difluoro-5,7-dimethyl-4-bora-3a,4a-diaza-s-indacene-3-hexadecanoic acid;
4,4-difluoro-5,7-dimethyl-4-bora-3a,4a-diaza-s-indacene-3-pentanoic acid;
4,4-difluoro-5,7-dimethyl-4-bora-3a,4a-diaza-s-indacene-3-undecanoic acid;
4,4-difluoro-5,7-diphenyl-4-bora-3a,4a-diaza-s-indacene-3-dodecanoic acid;
4,4-difluoro-5-methyl-4-bora-3a,4a-diaza-s-indacene-3-dodecanoic acid;
4,4-difluoro-5-octyl-4-bora-3a,4a-diaza-s-indacene-3-pentanoic acid;
4,4-difluoro-5-(4-phenyl-1,3-butadienyl)-4-bora-3a,4a-diaza-s-indacene-3-pentanoic acid;
4,4-difluoro-5-(4-phenyl-1,3-butadienyl)-4-bora-3a,4a-diaza-s-indacene-3-undecanoic acid;
4,4-difluoro-5-(2-thienyl)-4-bora-3a,4a-diaza-s-indacene-3-dodecanoic acid;
2-(4,4-difluoro-5,7-dimethyl-4-bora-3a,4a-diaza-s-indacene-3-dodecanoyl)-1-hexadecanoyl-sn-glycero-3-phosphocholine;
2-(4,4-difluoro-5,7-dimethyl-4-bora-3a,4a-diaza-s-indacene-3-pentanoyl)-1-hexadecanoyl-sn-glycero-3-phosphocholine;
2-(4,4-difluoro-5-methyl-4-bora-3a,4a-diaza-s-indacene-3-dodecanoyl)-1-hexadecanoyl-sn-glycero-3-phosphocholine;
2-(4,4-difluoro-5-octyl-4-bora-3a,4a-diaza-s-indacene-3-pentanoyl)-1-hexadecanoyl-sn-glycero-3-phosphocholine;
2-(4,4-difluoro-5-(4-phenyl-1,3-butadienyl)-4-bora-3a,4a-diaza-s-indacene-3-pentanoyl)-1-hexadecanoyl-sn-glycero-3-phosphocholine;
2-(4,4-difluoro-5,7-dimethyl-4-bora-3a,4a-diaza-s-indacene-3-pentanoyl)-1-hexadecanoyl-sn-glycero-3-phosphate;

N-(4,4-difluoro-5,7-dimethyl-4-bora-3a,4a-diaza-s-indacene-3-propionyl)-1,2-dihexadecanoyl-sn-glycero-3-phosphoethanolamine;
N-(4,4-difluoro-5,7-dimethyl-4-bora-3a,4a-diaza-s-indacene-3-propionyl)-1,2-dihexanoyl-sn-glycero-3-phosphoethanolamine
cholesteryl 4,4-difluoro-5,7-dimethyl-4-bora-3a,4a-diaza-s-indacene-3-dodecanoate;
cholesteryl 4,4-difluoro-5-(4-methoxyphenyl)-4-bora-3a,4a-diaza-s-indacene-3-undecanoate;
cholesteryl 4,4-difluoro-5-(2-pyrrolyl)-4-bora-3a,4a-diaza-s-indacene-3-undecanoate;
4,4-difluoro-1,3,5,7,8-pentamethyl-4-bora-3a,4a-diaza-s-indacene;
4,4-difluoro-1,3,5,7-tetramethyl-4-bora-3a,4a-diaza-s-indacene;
N-(4,4-Difluoro-5,7-Dimethyl-4-Bora-3a,4a-Diaza-s-Indacene-3-yl)Methyl)Iodoacetamide;
N-(4,4-Difluoro-1,3,5,7-Tetramethyl-4-Bora-3a,4a-Diaza-s-Indacene-2-yl)Iodoacetamide;
8-Bromomethyl-4,4-Difluoro-1,3,5,7-Tetramethyl-4-Bora-3a,4a-Diaza-s-Indacene
or pharmaceutically acceptable salts and/or ester derivatives thereof. In some embodiments, a pharmaceutically acceptable salt includes sodium, diammonium, and triethylammonium. In some embodiments, a pharmaceutically acceptable ester derivative includes succinimidyl ester and sulfosuccinimidyl ester derivatives.

Also contemplated herein are the compounds described in Ulrich, G. et al., *Angew. Chem. Int. Ed* 2008, 47: 1184-1201; Ziessel, R. et al., *New J. Chem.* 2007, 31: 496-501; and Loudet, A. and Burgess, K., *Chem. Rev.* 2007, 107: 4891-4932, all of which are incorporated by reference in their entirety herein.

A compound of Formula (IV), including salts thereof, can be prepared using known organic synthesis techniques and can be synthesized according to any of numerous possible synthetic routes. See, for example, Scheme 2.

Scheme 2

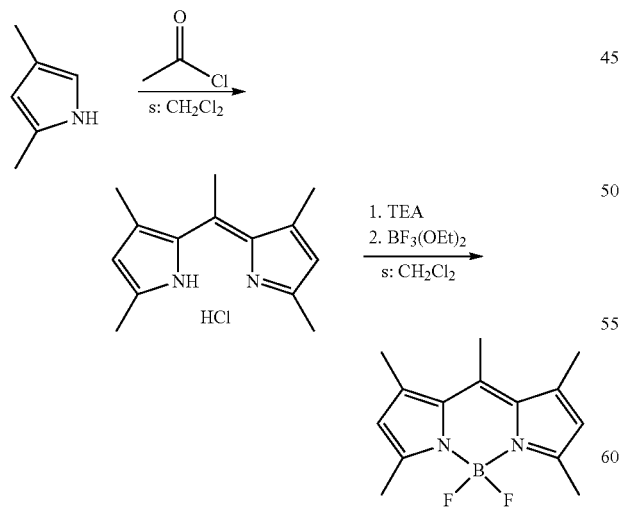

Alternatively, or additionally, a compound of Formula (IV) may be commercially is available (see, e.g., Life Technologies (Grand Island, N.Y.); Molecular Probes (Eugene, Oreg.); ATDBio (Southampton, UK)).

B. Compounds of Formula (V)

In some embodiments, the preparation of compounds of Formula (V) is contemplated:

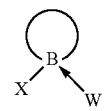

wherein:

is a BODIPY ligand system and X are defined as above; and W is a compound comprising a Lewis Base.

As is known to one of skill in the art, a Lewis base is any species that donates a pair of electrons to a Lewis acid to form a Lewis adduct. As used herein, W is a compound comprising a Lewis Base. One portion of W should have a high affinity for the group Y to abstract it from the boron (e.g., abstract a fluorine atom from the boron center). The counter-ion (i.e., the Lewis Base) replaces the Y group on the boron and should have a low affinity for the boron center. For example, W can be trifluoromethylsilyl triflate. The trifluoromethylsilyl group can abstract a fluorine from the boron center, replacing it with the triflate anion. Non-limiting examples of a group W include: trifluoromethylsilyl triflate and DMAP.

Non-limiting examples of Lewis Bases include: triflate, nonaflate, fluorosulfonate, tosylate, mesylate, DMAP, N,N-diisopropylethylamine (DIPEA), 1,8-diazabicycloundec-7-ene (DBU); N-methyl morpholine, N-methyl piperidine, pyridine, aniline, piperazine, piperidine, monoethanolamine (MEA), diethanolamine (DEA), 2-amino-2-methyl-1-propanol (AMP), 2-(2-aminoethylamino)ethanol (AEE), 1,5-diamino-3-oxapentane (DAOP), 1,5-bis(methylamino)-3-oxapentane (BMAP), 2-amino-2-hydroxymethyl-1,3-propanediol (Tris), diisopropanolamine (DIPA), diglycolamine (DGA), 2-n-propoxyethylamine, bis(2-methoxyethyl)amine, bis(2-ethoxyethyl)amine, 3-aminopropionitrile, 3,3'-iminodipropionitrile, aminoacetonitrile, hydroxy ethyl-ethylenediamine (HEED A), and 2,6-di-tert-butylpyridine.

In some embodiments, a compound W comprises a silane containing moiety such as alkylsilyl, haloalkylsilyl, alkynylsilyl, allylic silyl, propargylsilyl, benzylsilyl, silyl enol ethers, and silyl ketene acetals. In some embodiments, W comprises a trifluoromethylsilyl moiety. In certain of these embodiments, W comprises a trifluoromethylsilyl moiety and a Lewis Base (e.g., triflate).

In some embodiments, W is a trialkylsilyl triflate (e.g. trimethylsilyl triflate) or a dialkylaminopyridine (e.g. dimethylaminopyridine, DMAP).

Formula (V) can include, for example, the compound:

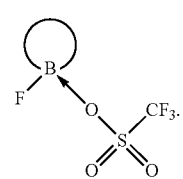

In some embodiments, a compound of Formula (V) can include the compound:

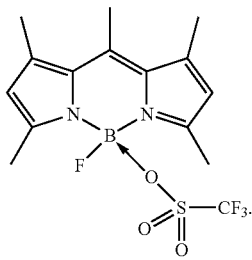

A compound of Formula (V) can be prepared by reacting a compound of Formula (IV):

with a compound W, as described above, to produce a compound of Formula (V).

In some embodiments, a ratio of 1:1 equivalents of a compound W to a compound of Formula (IV) can be used (e.g., 1.5:1; 2:1; 2.5:1; 3:1; 3.5:1; 4:1; 4.5:1; 5:1; 5.5:1; 6:1, at least 7:1, at least 8:1, at least 9:1, and at least 10:1). In some embodiments, a ratio from about 1:1 to about 5:1 equivalents of a compound W to a compound of Formula (IV) is used. In some embodiments, an excess of a compound W to a compound of Formula (IV) is used (e.g., at least about 1.5:1; at least about 2:1; at least about 2.5:1; at least about 3:1; at least about 3.5:1; at least about 4:1; at least about 4.5:1; at least about 5:1). In some embodiments, a ratio of about 5:1 equivalents of a compound W to a compound of Formula (IV) is used.

The preparation of a compound of Formula (V) can be performed at any reasonable temperature. For example, the reaction can be performed at temperatures which minimize acid-mediated degradation of the free pyrrole ligand. In some embodiments, the reaction is performed at a temperature from about 40° C. to about −80° C. In some embodiments, the reaction is performed at a temperature from about 30° C. to about −10° C. (e.g., about 25° C. to about −10° C.; about 15° C. to about −10° C.; about 10° C. to about −10° C.; about 5° C. to about −10° C.; about 0° C. to about −10° C.; about 25° C. to about −5° C.; about 25° C. to about 0° C.; about 15° C. to about −5° C.; about 10° C. to about 0° C.; and about 5° C. to about −5° C.).

The reaction time of the preparation of a compound of Formula (V) can range from about 30 seconds to about 5 minutes (e.g., about 30 seconds to about 4 minutes; about 30 seconds to about 3.5 minutes; about 30 seconds to about 3 minutes; about 30 seconds to about 2.5 minutes; about 30 seconds to about 2 minutes; about 30 seconds to about 1.5 minutes; about 30 seconds to about 1 minute; about 1 minute to about 5 minutes; about 1.5 minutes to about 5 minutes; about 2 minutes to about 5 minutes; about 2.5 minutes to about 5 minutes; about 3 minutes to about 5 minutes; about 3.5 minutes to about 5 minutes; about 4 minutes to about 5 minutes; about 1 minute to about 4 minutes; about 1.5 minutes to about 3.5 minutes; about 2 minutes to about 3 minutes; and about 1 minute to about 3 minutes). In some embodiments, the reaction time is about 2.5 minutes.

In some embodiments, a ratio of about 5:1 equivalents of a compound W to a compound of Formula (IV) is reacted at a temperature ranging from about 5° C. to about −5° C. for a time ranging from about 2 minutes to about 3 minutes to prepare a compound of Formula (V). For example, a ratio of no more than about 5:1 equivalents of a compound W to a compound of Formula (IV) can be reacted at a temperature of about 0° C. for about 2.5 minutes to prepare a compound of Formula (V).

A compound of Formula (V) can be used without further purification to prepare a compound of Formula (III). In some embodiments, the compound of Formula (V) is isolated and/or purified using known methods. See, e.g., Hudnall, T. W.; Gabbaï, F. P. *Chem. Commun.* 2008, 4596.

C. Compounds of Formula (III)

Also provided herein is the preparation of a compound of Formula (III):

or a pharmaceutically acceptable salt thereof, wherein

is a BODIPY ligand system and X is a halogen as defined above; and $R^1$ is a substituted or unsubstituted $C_{1-20}$ alkoxy or a substituted or unsubstituted $C_{1-20}$ alkynyl. In some embodiments, $R^1$ is an unsubstituted $C_{1-20}$ alkyl (e.g., $CH_3$). In some embodiments, $R^1$ is a —O-L-Z moiety as described above. In other embodiments, $R^1$ is a —$(C_2)$-L-Z moiety as described previously. In some embodiments, $R^1$ is a radiolabeled $C_{1-20}$ alkoxy (e.g., a $^{13}C$ labeled alkoxy compound such as O-$^{13}CH_3$).

In some embodiments, the compound of Formula (III) includes a compound of Formula (I) or Formula (II):

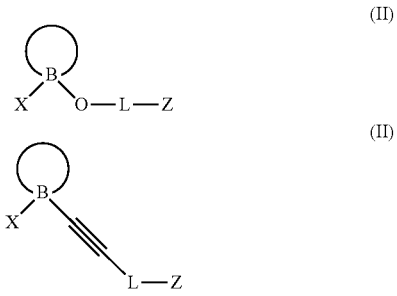

wherein:

is a BODIPY ligand system;
X is a halogen;
L is absent or a linker; and
Z is selected from the group consisting of: a group reactive with a biologically active molecule and a detectable agent; as defined above.
Non-limiting examples of a compound of Formula (II) include:
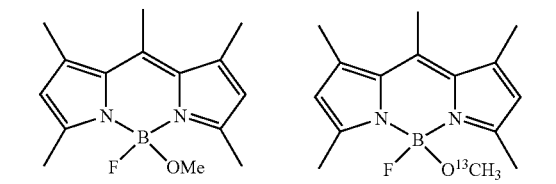
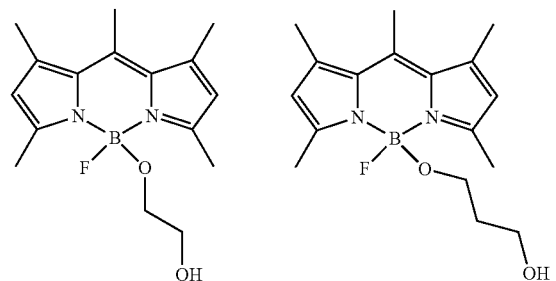
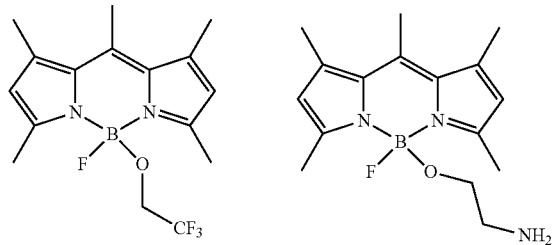
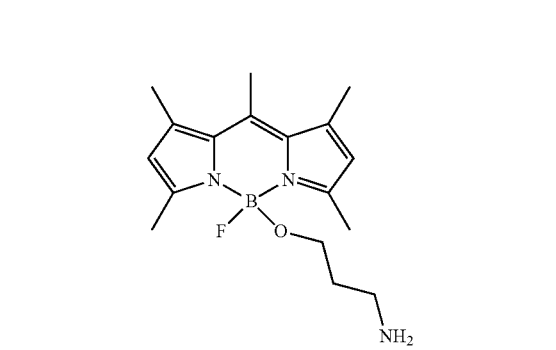
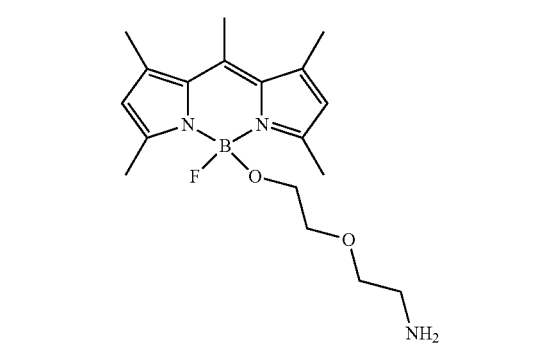
-continued
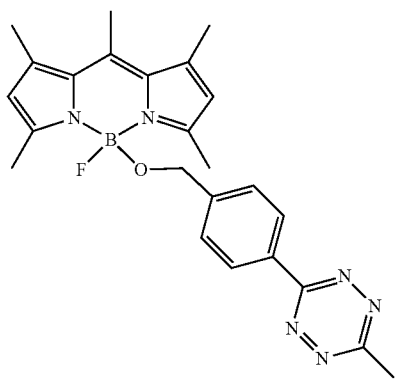
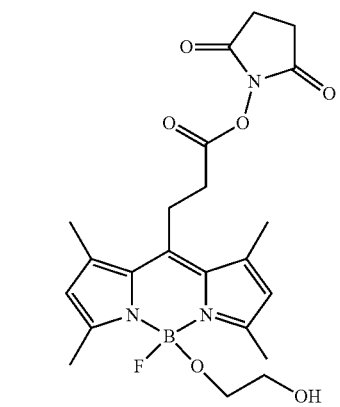
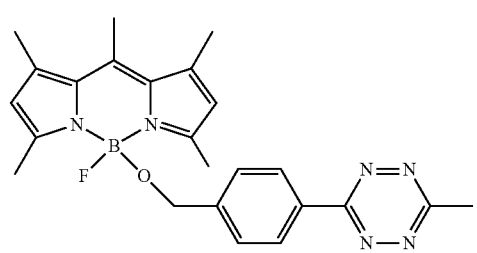
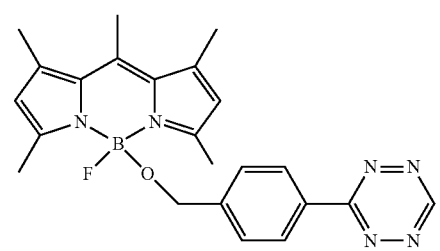
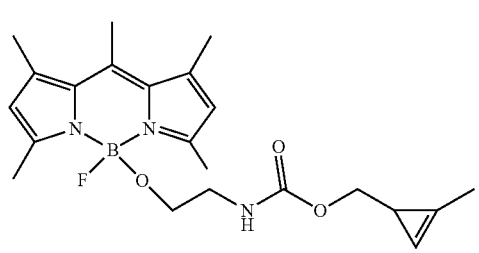

-continued
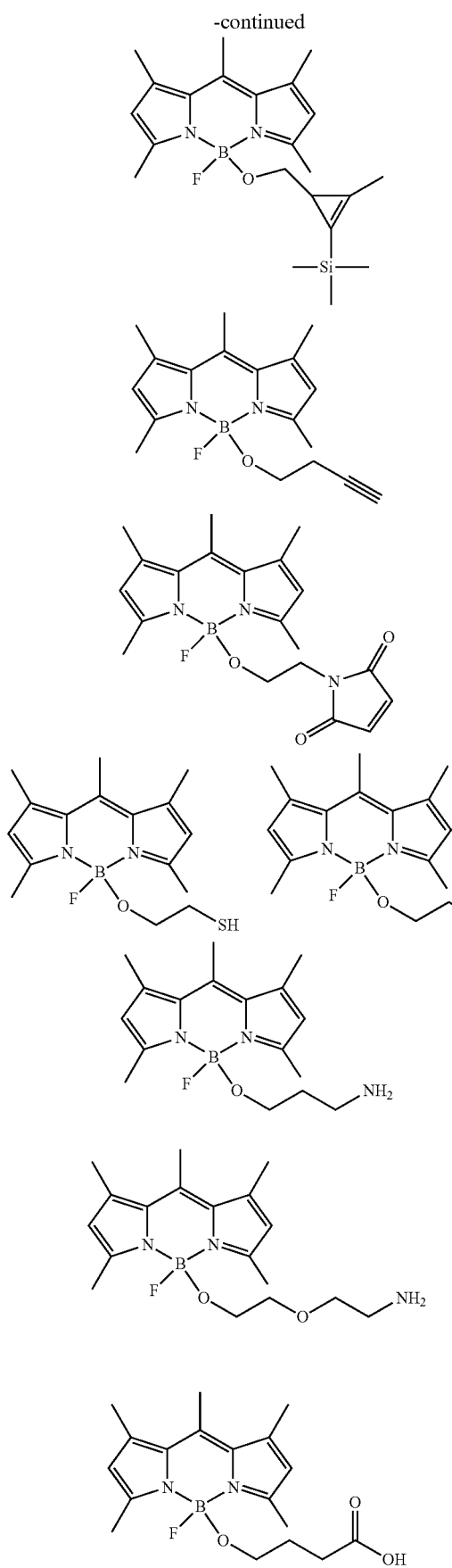
-continued
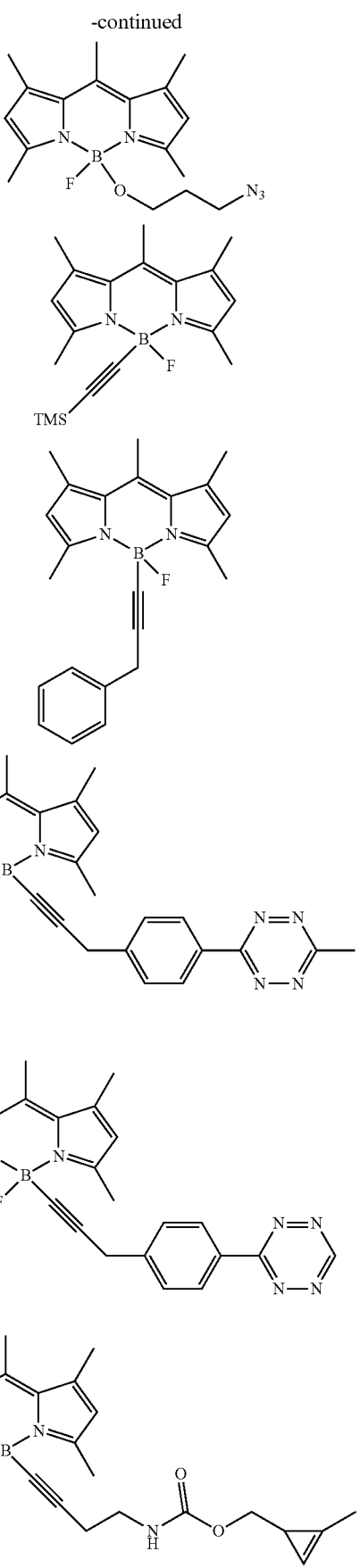

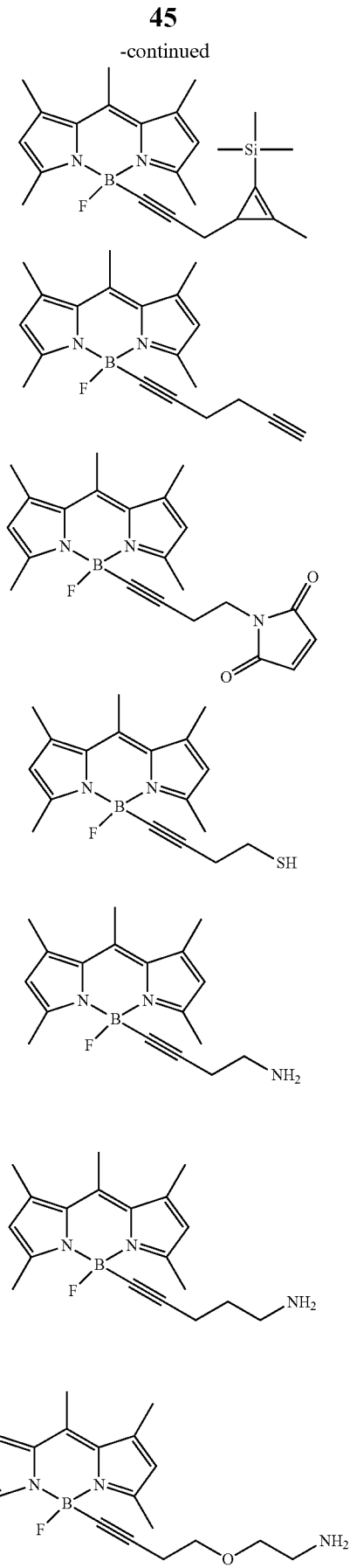

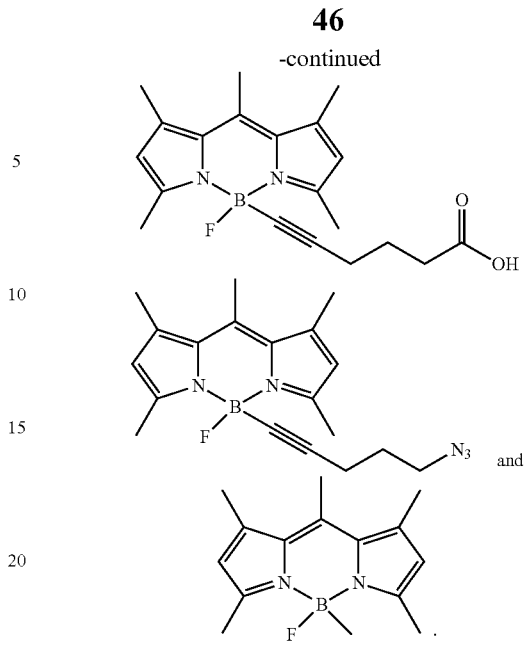

A compound of Formula (III) (e.g., a compound of Formula (I) or Formula (II)) can be prepared by reacting a compound of Formula (V) with a compound HR$^1$. In particular, a compound of Formula (V) can be reacted with any desired alcohol or alkyne compound to achieve substitution on the boron center of the BODIPY ligand system.

In some embodiments, an excess of a compound HR$^1$ is used in the reaction with a compound of Formula (V). For example, a ratio of at least about 2:1 equivalents of HR$^1$ to a compound of Formula (V) (e.g., at least about 3:1 equivalents; at least about 4:1 equivalents; at least about 5:1 equivalents; at least about 6:1 equivalents; at least about 7:1 equivalents; at least about 8:1 equivalents; at least about 9:1 equivalents; and at least about 10:1 equivalents). In some embodiments, a compound HR$^1$ is used in the reaction with a compound of Formula (V) at a ratio no greater than 1:1 equivalents of HR$^1$ to a compound of Formula (V) (e.g., no greater than about 1:2 equivalents; no greater than about 1:3 equivalents; no greater than about 1:4 equivalents; no greater than about 1:5 equivalents; no greater than about 1:6 equivalents; no greater than about 1:7 equivalents; no greater than about 1:8 equivalents; no greater than about 1:9 equivalents; and no greater than about 1:10 equivalents). Without being bound by theory, sub-stoichiometric amounts can be used with certain classes of alcohols, e.g., radiolabeled alcohols, high-boiling point alcohols, expensive alcohols, etc.

In addition to a compound of HR$^1$, a mild, non-nucleophilic base can be added to the reaction mixture. Non-limiting examples of such a base include, N,N-diisopropylethylamine (DIPEA), 1,8-diazabicycloundec-7-ene (DBU); N-methyl is morpholine, N-methyl piperidine, pyridine, aniline, piperazine, piperidine, monoethanolamine (MEA), diethanolamine (DEA), 2-amino-2-methyl-1-propanol (AMP), 2-(2-aminoethylamino)ethanol (AEE), 1,5-diamino-3-oxapentane (DAOP), 1,5-bis(methylamino)-3-oxapentane (BMAP), 2-amino-2-hydroxymethyl-1,3-propanediol (Tris), diisopropanolamine (DIPA), diglycolanmine (DGA), 2-n-propoxyethylamine, bis(2-methoxyethyl) amine, bis(2-ethoxyethyl)amine, 3-aminopropionitrile, 3,3'-iminodipropionitrile, aminoacetonitrile, hydroxy ethyl-ethylenediamine (HEED A), and 2,6-di-tert-butylpyridine. In some embodiments, DIPEA is added to the reaction mixture.

In some embodiments, prior to addition of HR$^1$, an intermediate alcohol quench of the excess of a compound W (e.g., TMSOTf) can be performed using an alcohol that differs from HR$^1$. Any sterically hindered alcohol can be used for the intermediate alcohol quench. In some embodiments, the alcohol is relatively easy to remove from the reaction mixture (e.g., has a low boiling point). For example, a tert-alcohol (e.g., tert-butanol) can be added prior to addition of HR$^1$. Without being bound by theory, such a step can be used when using smaller amounts of HR$^1$ in the reaction are desirable (e.g., when HR$^1$ is radiolabeled, expensive, and/or unstable).

The preparation of a compound of Formula (III) can be performed in a one-pot reaction.

Schemes 3 and 4 are illustrative examples of the preparation of compounds of Formula (I).

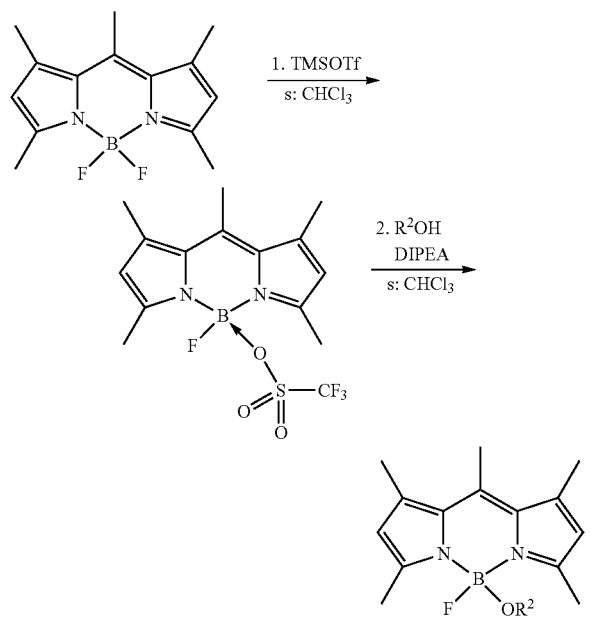

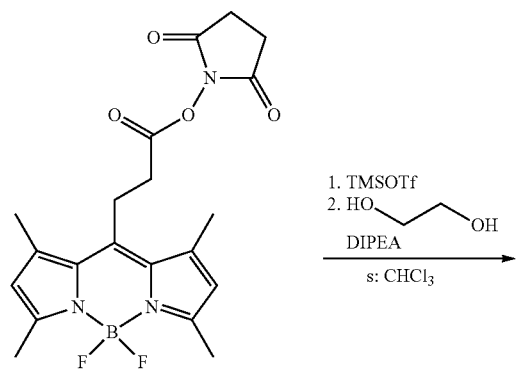

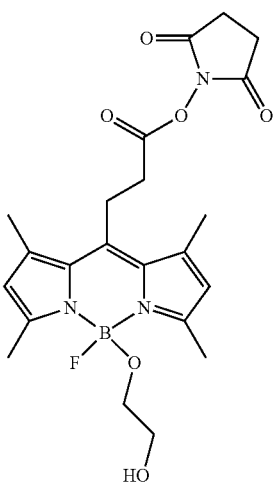

In some embodiments, the compound HR$^1$ can be activated prior to reaction with a compound of Formula (V). For example, the compound HR$^1$ can be activated through reaction with a Grignard Reagent (e.g., ethyl magnesium bromide).

In some embodiments, a compound of Formula (III) (e.g., a compound of Formula (I) or Formula (II)) can be prepared by reacting a compound of Formula (V) with an activated compound HR$^1$. In particular, a compound of Formula (V) can be reacted with an activated alkyne compound to achieve substitution on the boron center of the BODIPY ligand system.

In some embodiments, an excess of an activated compound HR$^1$ is used in the reaction with a compound of Formula (V). For example, a ratio of at least about 2:1 equivalents of an activated HR$^1$ to a compound of Formula (V) (e.g., at least about 3:1 equivalents; at least about 4:1 equivalents; at least about 5:1 equivalents; at least about 6:1 equivalents; at least about 7:1 equivalents; at least about 8:1 equivalents; at least about 9:1 equivalents; and at least about 10:1 equivalents). In some embodiments, a compound HR$^1$ is used in the reaction with a compound of Formula (V) at a ratio no greater than 1:1 equivalents of an activated HR$^1$ to a compound of Formula (V) (e.g., no greater than about 1:2 equivalents; no greater than about 1:3 equivalents; no greater than about 1:4 equivalents; no greater than about 1:5 equivalents; no greater than about 1:6 equivalents; no greater than about 1:7 equivalents; no greater than about 1:8 equivalents; no greater than about 1:9 equivalents; and no greater than about 1:10 equivalents. Without being bound by theory, sub-stoichiometric amounts can be used with certain classes of alkynes, e.g., radiolabeled alkynes.

In certain of these embodiments, the preparation of a compound of Formula (II) can be performed in a one-pot reaction.

Schemes 5 and 6 are illustrative examples of the preparation of compounds of Formula (III).

Scheme 5
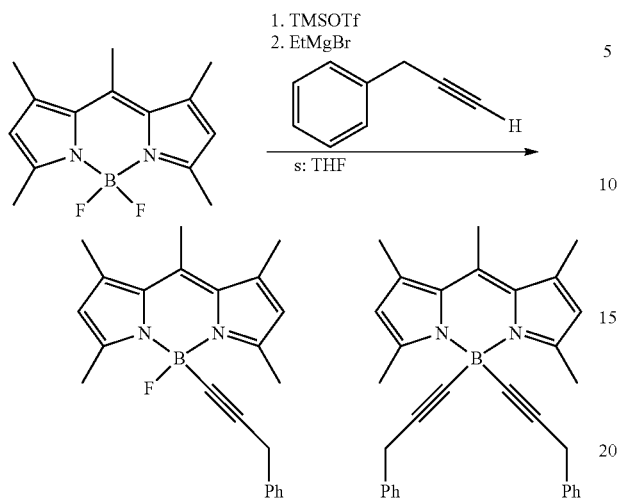
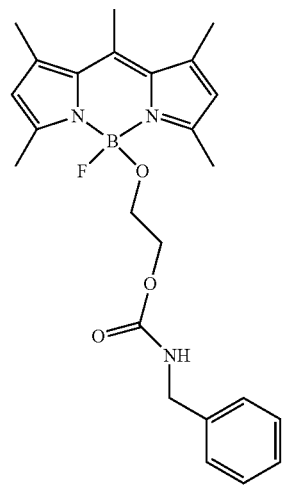
Scheme 6
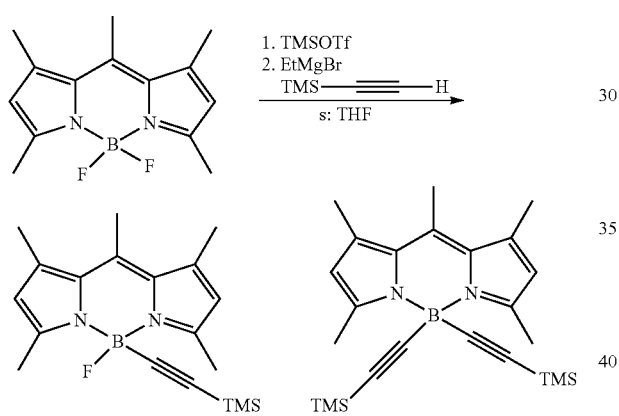
In some embodiments, a compound of Formula (III) can be further modified using standard protocols. For example, 1,1'-carbonyldiimidazole (CDI) can be coupled with a free primary alcohol of a compound of Formula (III). In some embodiments, the modification can be performed as shown in Schemes 7-9.
Scheme 7
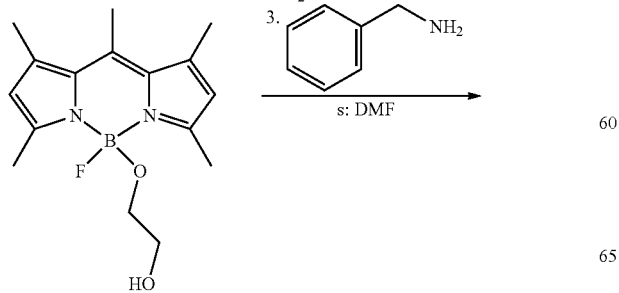
Scheme 8
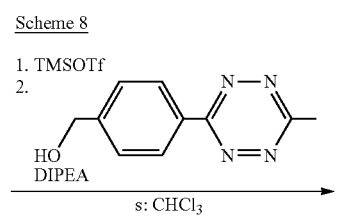
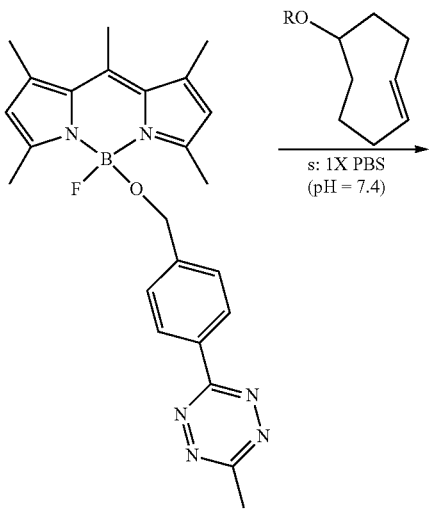

51
-continued

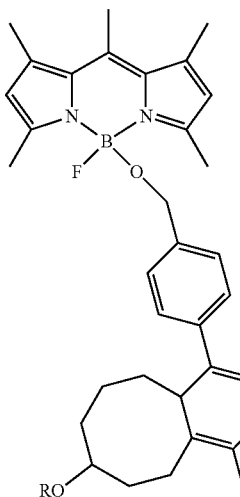

↓

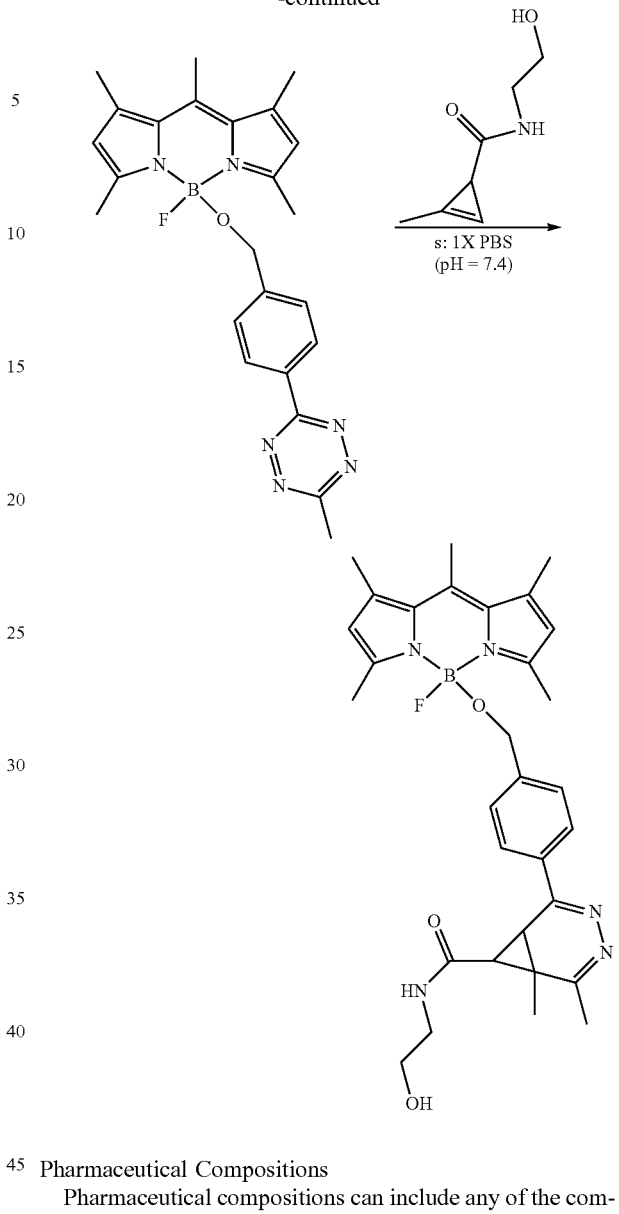

In Scheme 8, R can be any organic residue which does not react with the tetrazine moiety.

Scheme 9

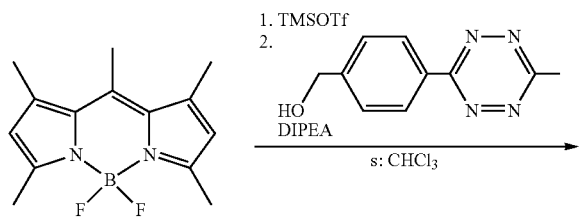

Pharmaceutical Compositions

Pharmaceutical compositions can include any of the compounds described previously, and can be Formulated as a pharmaceutical composition in accordance with routine procedures. As used herein, pharmaceutical compositions can include pharmaceutically acceptable salts or derivatives thereof. "Pharmaceutically acceptable" means that the agent can be administered to an animal without unacceptable adverse effects. A "pharmaceutically acceptable salt or derivative" means any pharmaceutically acceptable salt, ester, salt of an ester, or other derivative of composition that, upon administration to a recipient, is capable of providing (directly or indirectly) a composition of the present disclosure. Other derivatives are those that increase the bioavailability when administered to a mammal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the therapeutic or diagnostic compositions or compositions of this disclosure include counter ions derived from pharmaceutically acceptable inorganic and organic acids and bases known in the art, e.g., sodium, calcium, N-methylglutamine, lithium, magnesium, potassium, etc.

Pharmaceutical compositions can be administered by any route, including oral, intranasal, inhalation, or parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, compositions can be Formulated for any route of administration.

Typically, compositions for intravenous administration are solutions in sterile isotonic aqueous buffer. Where necessary, the composition may also include a is solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions comprise the therapeutic or diagnostic compositions of the present disclosure and pharmaceutically acceptable salts thereof, with any pharmaceutically acceptable ingredient, excipient, carrier, adjuvant or vehicle.

A pharmaceutical composition is preferably administered to the patient in the form of an injectable composition. The method of administering a therapeutic or diagnostic composition is preferably parenterally, meaning intravenously, intra-arterially, intrathecally, interstitially or intracavitarilly. Pharmaceutical compositions can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

Methods of Use

The compounds described herein can be imaged using methods known in the art. For example, imaging can be achieved in living animals, organs, or tissues, using e.g. fluorescence, near infrared (NIR), MR imaging (MRI), positron emission tomography (PET), single photon computerized tomography (SPECT), or other whole body imaging modalities based on the compound and the detectable agents associated with the compound. For example, a compound having a fluorescent detectable agent can be detected by traditional fluorescence imaging techniques allowing for the facile tracking of the compounds by fluorescence microscopy or flow cytometry using methods known in the art, e.g., as described in US 2005/0249668, the content of which is incorporated by reference in its entirety. In some embodiments, a compound having a radioactive agent (e.g., $^{18}F$) can be imaged using positron emission tomography (PET).

The compositions and methods described herein can be imaged using a variety of modalities that are known to one of skill in the art. Detection methods can include both imaging ex vivo and in vivo imaging methods, e.g., immunohistochemistry, bioluminescence imaging (BLI), Magnetic Resonance Imaging (MRI), positron emission tomography (PET), Single-photon emission computed tomography (SPECT), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required. In some embodiments, one or more imaging techniques can be used in the methods provided herein. For example, fluorescence, PET and/or SPECT imaging can be used.

In some embodiments, a compound as provided herein is imaged in vivo using PET or SPECT imaging. For example, the use of such methods permits the facile, real-time imaging and localization of cells or tissues labeled with a compound provided herein comprising a radioactive detectable agent. In some embodiments, a compound provided herein is imaged in vivo using laparoscopy and/or endomiscroscopy. For example, the use of laparoscopy permits the facile, real-time imaging and localization of cells or tissues labeled with a compound provided herein. In some embodiments, a compound can be imaged using fiber optic endomicroscopy.

With respect to in vitro imaging methods, the compounds and compositions described herein can be used in a variety of in vitro assays. An exemplary in vitro imaging method comprises: contacting a sample, for example, a biological sample (e.g., a cell), with one or more compounds provided herein; allowing the compound to interact with a biological target in the sample; optionally, removing unbound agents; illuminating the sample with light of a wavelength absorbable by a fluorophore of the agents; and detecting a signal emitted from fluorophore thereby to determine whether the agent has been activated by or bound to the biological target.

After a compound has been designed, synthesized, and optionally Formulated, it can be tested in vitro by one skilled in the art to assess its biological and performance characteristics. For instance, different types of cells grown in culture can be used to assess the biological and performance characteristics of the compound. Cellular uptake, binding or cellular localization of the agent can be assessed using techniques known in the art, including, for example, fluorescent microscopy, fluorescence-activated cell sorting (FACS) analysis, immunohistochemistry, immunoprecipitation, in situ hybridization and Forster resonance energy transfer (FRET) or fluorescence resonance energy transfer.

By way of example, the compound can be contacted with a sample for a period of time and then washed to remove any free compound. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples can also be used in a similar manner to assess the biological and performance characteristics of the compounds. Other detection methods including, but not limited to flow cytometry, immunoassays, hybridization assays, and microarray analysis can also be used.

EXAMPLES

The invention is further described in the following examples, which do not limit the scope of the invention described in the claims.

Example 1

Chemical Synthesis—General Methods

Reagents & Equipment

Reagents were purchased from Chem-Impex International, Aldrich, Fluka, and Sigma-Aldrich Co. and used without further purification unless otherwise noted. All solvents for syntheses were anhydrous. Thin layer chromatography was performed with precoated aluminum-backed TLC plates obtained from VWR: Aluminum Oxide 60, Neutral F254 & Silica Gel 60, Neutral F254. Visualization of TLC plates was performed with ninhydrin, iodine, or an UVGL-25 Compact IJV Lamp 254/365 UV (UVP 115V~60 Hz/0.16 Amps). Purifications were either performed with aluminum oxide (Brockmann 1, Sigma-Aldrich), silica (Silicycle), or on a Biotage Isolera 4 Purification System equipped with a 200-400 nm diode array detector. For flash purifications, Biotage SNAP Flash Chromatography Cartridges were used (KP-C18-Sil & KP-NH).

Analytical LC/MS was performed on a Waters HPLC/MS system (Waters 2545 Binary Gradient Module, 3100 Mass Detector, 2998 photodiode array detector, 2424 evaporative light scattering detector, 2475 multichannel fluorescence detector), operated by Masslynx software with Waters Xterra columns (C18, 5 um, 4.6×50 mm) using a binary solvent system (0.1% TFA in water and acetonitrile). Proton and carbon nuclear magnetic resonance ('H and '$^3$C NMR spectra) were recorded on a Varian AS-400 (400 MHz) spectrometer. Chemical shifts for protons are reported in parts per million (ppm) and are referenced to residual solvent peaks for $C_6H_6$ (7.16 ppm), $CHCl_3$ (7.26 ppm), and $CH_3CN$ (1.94 ppm). Data is reported as follows: chemical shift, integration, multiplicity (s=singlet, d=doublet, t=triplet, m=multiplet), and coupling constants (Hz). High-resolution mass-spectra were performed on a Bruker Daltonics APEXIV 4.7 Tesla Fourier Transform Ion Cyclotron Resonance Mass Spectrometer (FT-ICR-MS), with ESI (Electro Spray Ion) source.

Literature Compounds 1,3,5,7,8-Pentamethyl BODIPY (AMC1094), di-methoxy BODIPY (AMC1106), and (4-(6-methyl-1,2,4,5-terazin-3-yl)phenyl)methanol (AMC1088) were synthesized according to standard literature procedures (see, e.g., Tahtaoui, C.; Thomas, C.; Rohmer, F.; Klotz, P.; Duportail, G.; Mély, Y.; Bonnet, D.; Hibert, M. *J. Org. Chem.* 2007, 72, 269-272; and Yang, J.; Šečkutė, J.; Cole, C. M.; Devaraj, N. K. *Angew. Chem. Int. Ed* 2012, n/a-n/a).

Example 2

General Procedure A

In a round-bottom flask, (1 eq) 1,3,5,7,8-pentamethyl BODIPY was dissolved in $CHCl_3$. This solution was chilled at 0° C. on an ice-water bath and, under stirring, TMSOTf (5 eq) was added from a 10% stock-solution (v/v) in $CHCl_3$. The reaction was allowed to proceed for two minutes and thirty seconds. Then, a premixed solution of alcohol (~100 eq) and DIPEA (10 eq) was rapidly injected into the reaction mixture. The mixture was then partitioned between 1:1 $CH_2Cl_2:H_2O$. The organics were washed 3× with $ddH_2O$+ 10% $NaCl_{(sat)}$, dried over $Na_2SO_4$, gravity filtered, and solvents removed in vacuo at room temperature. All purifications were performed immediately after obtaining the dry, crude product.

Example 3

Preparation of 5-fluoro-5-methoxy-1,3,7,9,10-pentamethyl-5H-dipyrrolo[1,2-c:2',1'-f][1,3,2]diazaborinin-4-ium-5-uide (AMC1028)

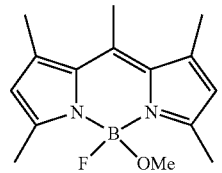

General procedure A (Example 2) was followed using methanol as the alcohol. Purified on aluminum oxide column (100% Toluene→10:1 Toluene:MeCN) yielding an orange powder (14 mg, 0.051 mmol, 46%). HRMS: $C_{15}H_{20}BFN_2O$ [M+Na]$^+$ Expected: 297.1558, Found: 297.1550/[M-F]$^+$ Calculated: 255.1676, Found: 255.1665. $^{13}C$ NMR (101 MHz, $c_6d_6$) 154.08 (s), 141.42 (s), 139.75 (s), 133.17 (s), 121.25 (s), 49.12 (d, J=6.9 Hz), 17.22 (s), 16.07 (s), 14.75 (d, J=2.6 Hz). $^1H$ NMR (400 MHz, $C_6D_6$) ?5.76 (s, 2H), 3.11 (s, 3H), 2.66 (s, 6H), 1.99 (s, 6H), 1.87 (s, 3H).

Example 4

Preparation of 5-fluoro-5-(2-hydroxyethoxy)-1,3,7,9,10-pentamethyl-5H-dipyrrolo[1,2-c:2',1'-f][1,3,2]diazaborinin-4-ium-5-uide (AMC1029)

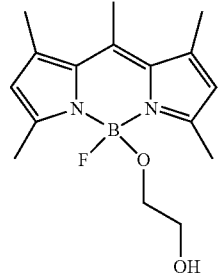

General procedure A (Example 2) was followed using ethylene glycol as the alcohol. Purified on aluminum-oxide column (1:1 Toluene:MeCN→1:5 Toluene:MeCN+1% MeOH) yielding an orange powder (20 mg, 0.066 mmol, 43%). HRMS: $C_{16}H_{22}BFN_2O_2$ [M+Na]$^+$ Calculated: 327.1664, Found: 327.1673. $^{13}C$ NMR (101 MHz, $C_6D_6$) 154.34 (s), 141.76 (s), 140.26 (s), 133.32 (s), 121.72 (s), 63.93 (s), 63.39 (d, J=5.7 Hz), 17.52 (s), 16.39 (s), 15.12 (d, J=2.8 Hz).

Example 5

Preparation of 5-fluoro-5-(3-hydroxypropoxy)-1,3,7,9,10-pentamethyl-5H-dipyrrolo[1,2-c:2',1'-f][1,3,2]diazaborinin-4-ium-5-uide (AMC1073)

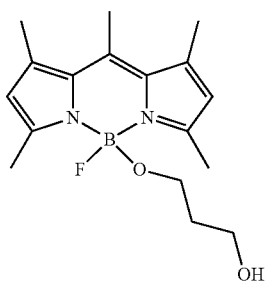

General procedure A (Example 2) was followed using propylene glycol as the alcohol. Purified on aluminum oxide column (5:1 Toluene:MeCN→1:5 Toluene:MeCN +1% MeOH) yielding an orange powder (22 mg, 0.069 mmol, 45%). HRMS: $C_{17}H_{24}BFN_2O_2$ [M+Na]$^+$ Calculated: 341.1821, Found: 341.1813. $^1$H NMR (400 MHz, $C_6D_6$) δ 5.74 (s, 2H), 3.80 (dd, J=10.4, 5.2, 2H), 3.36 (t, J=5.3, 1H), 3.21 (t, J=5.6, 2H), 2.63 (s, 6H), 1.98 (s, 6H), 1.86 (s, 3H), 1.61-1.55 (m, 2H). $^{13}$C NMR (101 MHz, $C_6D_6$) δ 154.11, 141.39, 139.92, 133.05, 128.30, 128.06, 127.82, 121.41, 63.37, 61.97, 61.91, 33.95, 17.18, 16.06, 14.80, 14.77.

Example 6

Preparation of 5-fluoro-1,3,7,9,10-pentamethyl-5-(2,2,2-trifluoroethoxy)-5H-dipyrrolo[1,2-c:2',1'-f][1,3,2]diazaborinin-4-ium-5-uide (AMC1096)

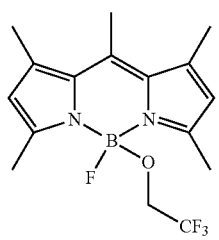

General procedure A (Example 2) was followed using trifluoroethanol as the alcohol. Purified on C18 Biotage cartridge (95:5 H$_2$O:MeCN→5:95 H$_2$O:MeCN) yielding an orange powder (15 mg, 0.044 mmol, 38%). HRMS: $C_{16}H_{19}BF_4N_2O$ [M+Na]$^+$ Calculated: 365.1432, Found: 365.1429. $^1$H NMR (400 MHz, CDCl$_3$) 6.07 (s, 2H), 3.25 (q, J=9.3 Hz, 2H), 2.59 (s, 3H), 2.52 (s, 6H), 2.42 (s, 6H). $^{13}$C NMR (101 MHz, cdcl$_3$) 154.34 (s), 141.35 (s), 140.94 (s), 132.68 (s), 128.29-127.55 (m), 121.73 (s), 60.97 (qd, J=34.5, 7.4 Hz), 17.57 (s), 16.58 (s), 14.48 (d, J=2.8 Hz).

Example 7

Preparation of 5-(2-aminoethoxy)-5-fluoro-1,3,7,9,10-pentamethyl-5H-dipyrrolo[1,2-c:2',1'-f][1,3,2]diazaborinin-4-ium-5-uide (AMC1097)

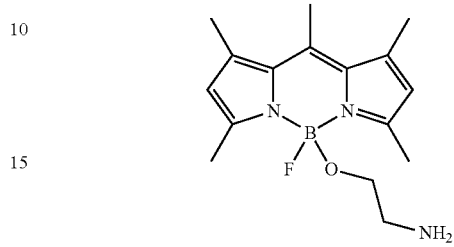

General procedure A (Example 2) was followed using ethanolamine as the alcohol. Purified on a KP-NH Biotage cartridge (9:1 Toluene:MeCN→1:3 Toluene:MeCN) yielding an orange powder (32 mg, 0.1055 mmol, 70%). HRMS $^1$H NMR (400 MHz, $C_6D_6$) 5.76 (s, 1H), 3.07 (t, J=5.3 Hz, 1H), 2.80-2.61 (m, 5H), 2.00 (s, 4H), 1.88 (s, 2H), 1.15 (s, 2H).

Example 8

Preparation of 5-fluoro-1,3,7,9,10-pentamethyl-5-((4-(6-methyl-1,2,4,5-tetrazin-3-yl)benzyl)oxy)-5H-dipyrrolo[1,2-c:2',1'-f]i[1,3,2]diazaborinin-4-ium-5-uide (AMC1090) (General Synthesis B)

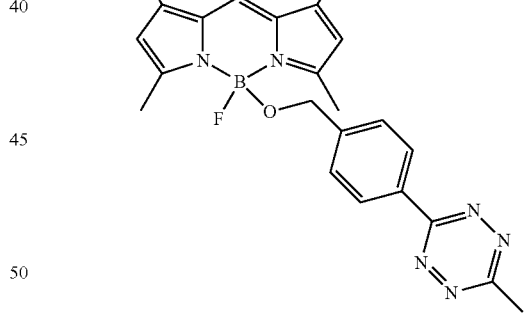

To AMC1094 (5.4 mg, 0.0206 mmol, 1.0 eq) in 4 mL CHCl$_3$ was added TMSOTf from a 10% stock solution in CHCl$_3$ (110 μL, 0.06181 mmol, 3.0 eq) under stirring at 0° C. After three minutes activation, the reaction was rapidly quenched with (4-(6-methyl-1,2,4,5-terazin-3-yl)phenyl)methanol (25.0 mg, 0.1237 mmol, 6.0 eq) and DIPEA (22 μL, 0.1236 mmol, 6.0 eq) in 4 mL CHCl$_3$. The reaction mixture was allowed to warm to room temperature over 15 min and then 20 mL 1:1 CH$_2$Cl$_2$:H$_2$O was added. Subsequently, the organic layer was washed 3× with 20 mL H$_2$O+10% NaCl$_{(sat)}$. The organic layer was dried over Na$_2$SO$_4$, gravity filtered, and solvents were removed in vacuo at room temperature. Purification was performed on an aluminum oxide column (10:1 Toluene:MeCN→1:1

Toluene:MeCN) yielding a red-orange powder (2.2 mg) HRMS: C$_{24}$H$_{26}$BFN$_6$O [M+Na]$^+$ Calculated: 467.2152, Found: 467.2150.

Example 9

Preparation of 10-(3-((2,5-dioxopyrrolidin-1-yl)oxy)-3-oxopropyl)-5-fluoro-5-(2-hydroxyethoxy)-1,3,7,9-tetramethyl-5H-dipyrrolo[1,2-c:2',1'-f][1,3,2]diazaborinin-4-ium-5-uide (AMC1092) (monoalkoxy BODIPY Synthesis C)

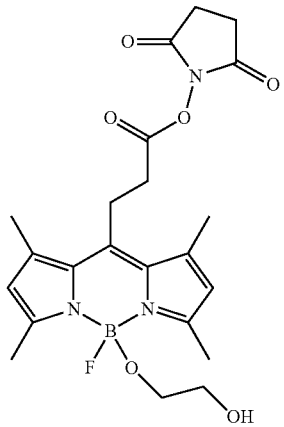

To difluoro NHS ester BODIPY (10 mg, 0.02457 mmol, 1.0 eq) in 15 mL CHCl$_3$ under stirring at 0° C. was added a 10% TMSOTf stock solution in CHCl$_3$ (220 µL, 0.1129 mmol, 5.0 eq). After a one minute activation time, the solution was rapidly quenched with a mixture of ethylene glycol (69 µL, 1.2285 mmol, 50.0 eq) and DIPEA (26 µL, 0.1474 mmol, 6.0 eq). The crude reaction mixture was partitioned in 50 mL 1:1 2-methyl tetrahydrofuran:H$_2$O. The organic layer was washed 3× with 50 mL H$_2$O+10% NaCl$_{(sat)}$, dried over Na$_2$SO$_4$, gravity filtered, and all solvents were removed in vacuo at room temperature. The compound was purified on silica gel (1:1 Toluene:MeCN→1:10 Tol:MeCN) yielding the title compound as a red-orange powder (4 mg). HRMS: C$_{22}$H$_{27}$BFN$_3$O$_6$ [M+Na]$^+$ Calculated: 482.1884, Found: 482.1890.

Example 10

General Procedure D

For all reactions, a fresh ~2 M solution of ethyl magnesium bromide was prepared by carefully adding bromoethane (4.06 mL, 54.9 mmol, 1.0 eq) to a solution of magnesium turnings (1.60 gr, 65.8 mmol, 1.2 eq) in 1THF (26.0 mL).

A. Preparation of 5-fluoro-1,3,7,9,10-pentamethyl-5-((trimethylsilyl)ethynyl)-5H-dipyrrolo[1,2-c:2',1'-1f][1,3,2]diazaborinin-4-ium-5-uide

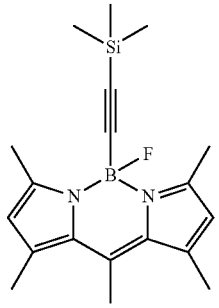

Part A.

In a 10 mL microwave vial, ~2 M ethyl magnesium bromide (0.500 mL, 1.01 mmol, 13.0 eq) was slowly added to a solution of TMS acetylene (217 µL, 1.53 mmol, 20.0 eq) dissolved 2 mL THF. After ~10 minutes, this was used as a stock solution for the next step, under the assumption of quantitative conversion to the expected acetylide ion.

In a 50 mL flask, AMC1094 (20.0 mg, 0.0763 mmol, 1.0 eq) was dissolved in 20 mL of CH$_2$Cl$_2$. Under vigorous stirring at 0° C., TMSOTf (60 µL, 0.382 mmol, 5.0 eq) was added from a 10% v/v TMSOTf stock in CH$_2$Cl$_2$. After a 2 minute 30 second activation, the entirety of the acetylide stock solution (1.01 mmol, 13.3 eq) from Part A was rapidly injected and the reaction was allowed to warm to room temperature. The crude reaction is solution was quenched with 5 mL ddH$_2$O and then partitioned between 100 mL 1:1 CH$_2$Cl$_2$:ddH$_2$O. The organic layer was washed 3× with 20 mL ddH$_2$O+NaCl (sat). The organic layer was dried over Na$_2$SO$_4$, gravity filtered, and all solvents were removed in vacuo at room temperature.

B. Preparation of 5-fluoro-1,3,7,9,10-pentamethyl-5-(3-phenylprop-1-yn-1-yl)-5H-dipyrrolo[1,2-c:2',1'-f][,3,2]diazaborinin-4-ium-5-uide

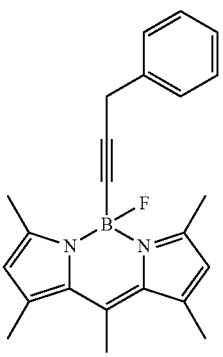

Part A.

In a 10 mL microwave vial, ~2 M ethyl magnesium bromide (0.500 mL, 1.01 mmol, 13.0 eq) was slowly added to a solution of 3-phenyl-1-propyne (190 µL, 1.53 mmol, 20.0 eq) dissolved 2 mL THF. After ~10 minutes, this solution was used as the quenching stock for the next step, under the assumption of quantitative conversion to the expected acetylide ion.

Part B.

In a 50 mL flask, AMC1094 (20.0 mg, 0.0763 mmol, 1.0 eq) was dissolved in 20 mL of $CH_2Cl_2$. Under vigorous stirring at 0° C., TMSOTf (60 μL, 0.382 mmol, 5.0 eq) was added from a 10% v/v TMSOTf stock in $CH_2Cl_2$. After a 2 minute 30 second activation, the entirety of the acetylide stock solution (1.01 mmol, 13.3 eq) from Part A was rapidly injected and the reaction was allowed to warm to room temperature. The crude reaction solution was quenched with 5 mL dd$H_2O$ and then partitioned between 100 mL 1:1 $CH_2Cl_2$:dd$H_2O$. The organic layer was washed 3× with 20 mL dd$H_2O$+NaCl (sat). The organic layer was dried over $Na_2SO_4$, gravity filtered, and all solvents were removed in vacuo at room temperature.

Example 11

Physical Characterization

A. Optical Attributes, Solubility, and Lipophilicity Data

Various characteristics of the compounds prepared in Examples 3-9 were explored, including determinations of partition coefficients, solubility, quantum yields, spectral properties, and molar extinction coefficient calculations. Partition coefficient (Log P) was determined via the shake-flask method by partitioning a saturated solution of the probes in 1×PBS with octanol. Solubility was determined in 1×PBS (pH 7.3) from the concentration of a saturated solution of each probe. Quantum yield was determined in dd$H_2O$ using Fluorescein in 0.1M NaOH as a reference. Spectral properties ($\lambda_{max}$em and $\lambda_{max}$abs) were determined in dd$H_2O$ or DMSO. Molar extinction coefficient (ε) was determined according to the Beer-Lambert law in triplicate using a quartz cuvette. Values are expressed as $M^{-1}cm^{-1}$. Results of these experiments are shown in Table 1.

TABLE 1

| Structure | LogP | Solubility | $\Phi_{fl}$ | $\lambda_{max}$em | $\lambda_{max}$abs | ε |
|---|---|---|---|---|---|---|
| (BODIPY, F/OMe) | 1.4 | 24 μM | 0.327 | 520 nm[a] | 492 nm[a] | 70,905[a] |
| (BODIPY, F/OCH$_2$CF$_3$) | n/a | 3 | | 510 nm[a] 513 nm[c] | 491 nm[a] 495 nm[b] | 54,758[a] 79,613[b] |
| (BODIPY, F/OCH$_2$CH$_2$OH) | 2.2 | 122 | 0.472 | 504 nm[a] | 491 nm[a] 495 nm[b] | 66,313[a] 77,175[b] |
| (BODIPY, F/OCH$_2$CH$_2$CH$_2$OH) | 2.2 | 48 | 0.352 | 504 nm[a] | 491 nm[a] | 66,703[a] |

TABLE 1-continued

| Structure | LogP | Solubility | $\Phi_{fl}$ | $\lambda_{max}$em | $\lambda_{max}$abs | $\in$ |
|---|---|---|---|---|---|---|
| (BODIPY with F, O-CH₂CH₂-NH₂) | 0.32 | 450 | | | 492 nm$^a$ | 50,624$^a$ |
| (BODIPY with MeO, OMe) | ~2.4 | n/a | 0.349 | 506 nm$^a$ | 491 nm$^a$ | 71,280$^a$ |
| (BODIPY with F, F) | n/a | 3 | | 513 nm$^c$ | 457 nm$^a$ (broad) 494 nm$^c$ | 10,256$^a$ 86,549$^c$ |

$^a$Value measured in ddH$_2$O
$^b$Value measured in methanol
$^c$Value measured in DMSO As can be seen in Table 1, the spectral properties of the mono-alkoxy BODIPY derivatives in water are competitive to those measured for the di-alkoxy compounds.

B. Stability Tests on Plate-Reader

Room-temperature stability of the compounds prepared above was tested in 1× PBS (pH 7.4) and a standard cell-imagining and growth media, phenol-red free RPMI 1640+10% Fetal Bovine Serium (FBS). Experiments were performed in quadruple replicates on a high throughput plate reader with fluorescent readout tuned to the emission profile of BODIPY. Stability tests were performed on a TECAN Safire 2 multi-well plate reader.

From 10 mM DMSO stock solutions, 10 µM dilutions of the title BODIPY derivatives and Fluorescein were prepared in 1×PBS (pH=7.4) and cell imaging media [RPMI 1640 (+) 10% FBS & (−) phenol red]. 30 µL of replicates were pinned into black, flat-bottom 364-well plates (CORNING). Fixed fluorescence intensity readings were acquired over 80 hours under constant instrument settings. Excitation and emission wavelengths selected for monitoring were optimized for BODIPY analogues ($\lambda_{exc}$=490 nm, $\lambda_{emm}$=512 nm). In between reads, plates were stored at room temperature and protected from light. Note that AMC1094 and AMC1096 were analyzed in 1:1 1×PBS:DMF.

Figure 2:
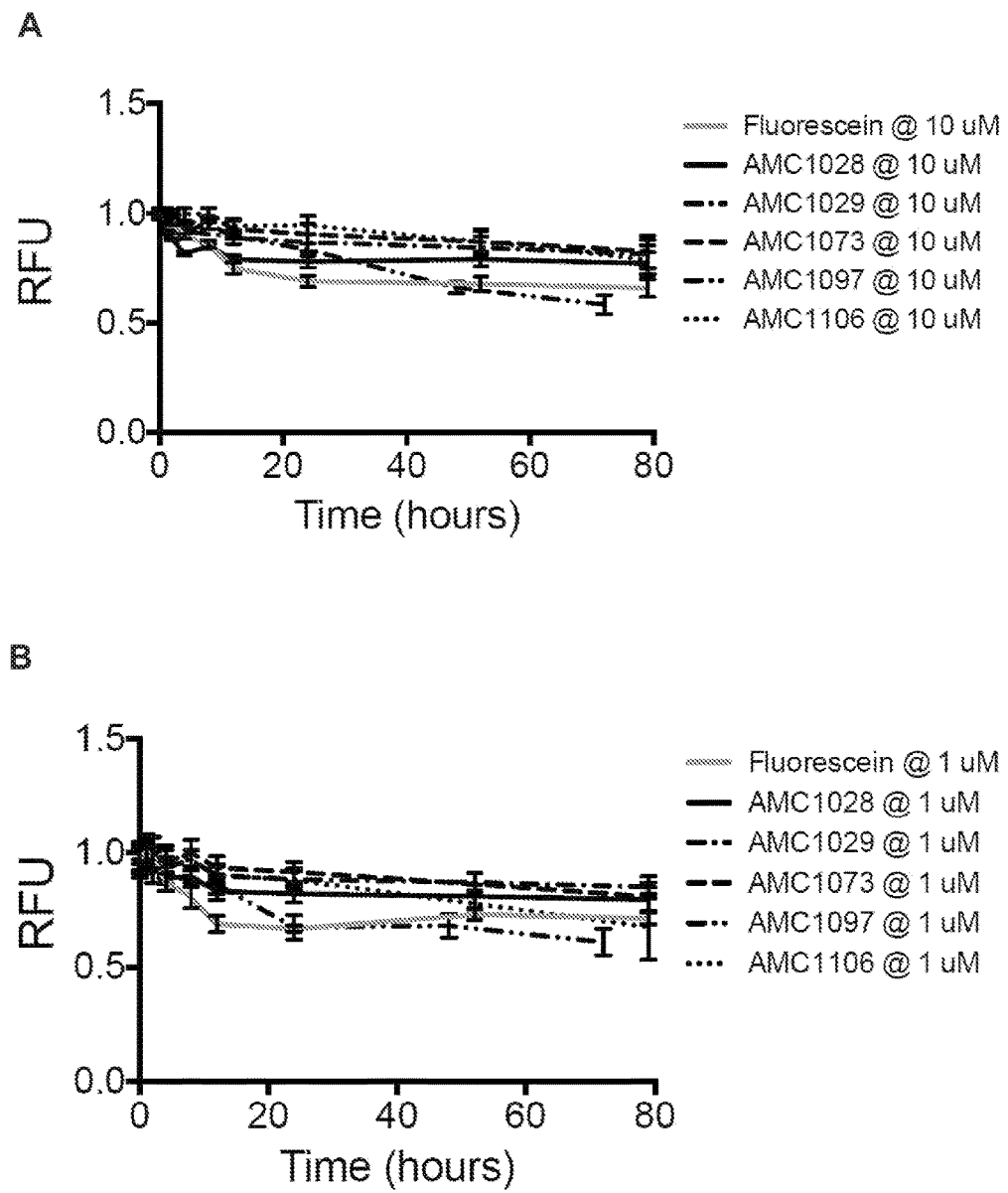
FIG. 2 is a line drawing illustrating the stability of mono-alkoxy BODIPY derivatives in standard cell-imaging and growth media at room temperature over 80 hours.

As shown in FIGS. 1 and 2, the stability of the mono-alkoxy derivatives were competitive with Fluorescein in aqueous buffer (FIG. 1) and proved to be more stable in the cellular media (FIG. 2). As can be also seen in these two figures, the dimethoxy BODIPY control compound AMC1106 initially tracks on par with our derivatives until eventually reaching worse fluorescence signal stability.

C. Stability Tests on Analytical LC/MS

To investigate the persistence of the chemical integrity of the dyes, a 24-hour stability study on the BODIPY derivatives was performed in 1×PBS using a LC/MS outfitted with an ultra-sensitive fluorescence detector.

From 10 mM DMSO stock solutions, 10 µM dilutions of the title BODIPY derivatives of Examples 3-9 were prepared in 1×PBS (pH=7.4). Replicates were stored, protected from light, either at room-temperature or in a sterile incubator (37° C., 5% CO$_2$). Over 24 hours, neat aliquots were taken from these solutions at standardized time points and analyzed on the analytical LC/MS system described in "Chemical Syntheses—Reagents and Equipment". Waters HPLC/MS system (Waters 2545 Binary Gradient Module, 3100 Mass Detector, 2998 photodiode array detector, 2424 evaporative light scattering detector, 2475 multichannel fluorescence detector), operated by Masslynx software with Waters Xterra columns (C18, 5 um, 4.6×50 mm) using a binary solvent system (0.1% TFA in water and acetonitrile). The multi-wavelength fluorescence detector settings were optimized for monitoring BODIPY fluorescence ($\lambda_{exc}$=490 nm, $\lambda_{emm}$=512 nm). Instrument gain and EUFS settings were maintained as constant values across runs during the time-course experiment.

Figure 3:
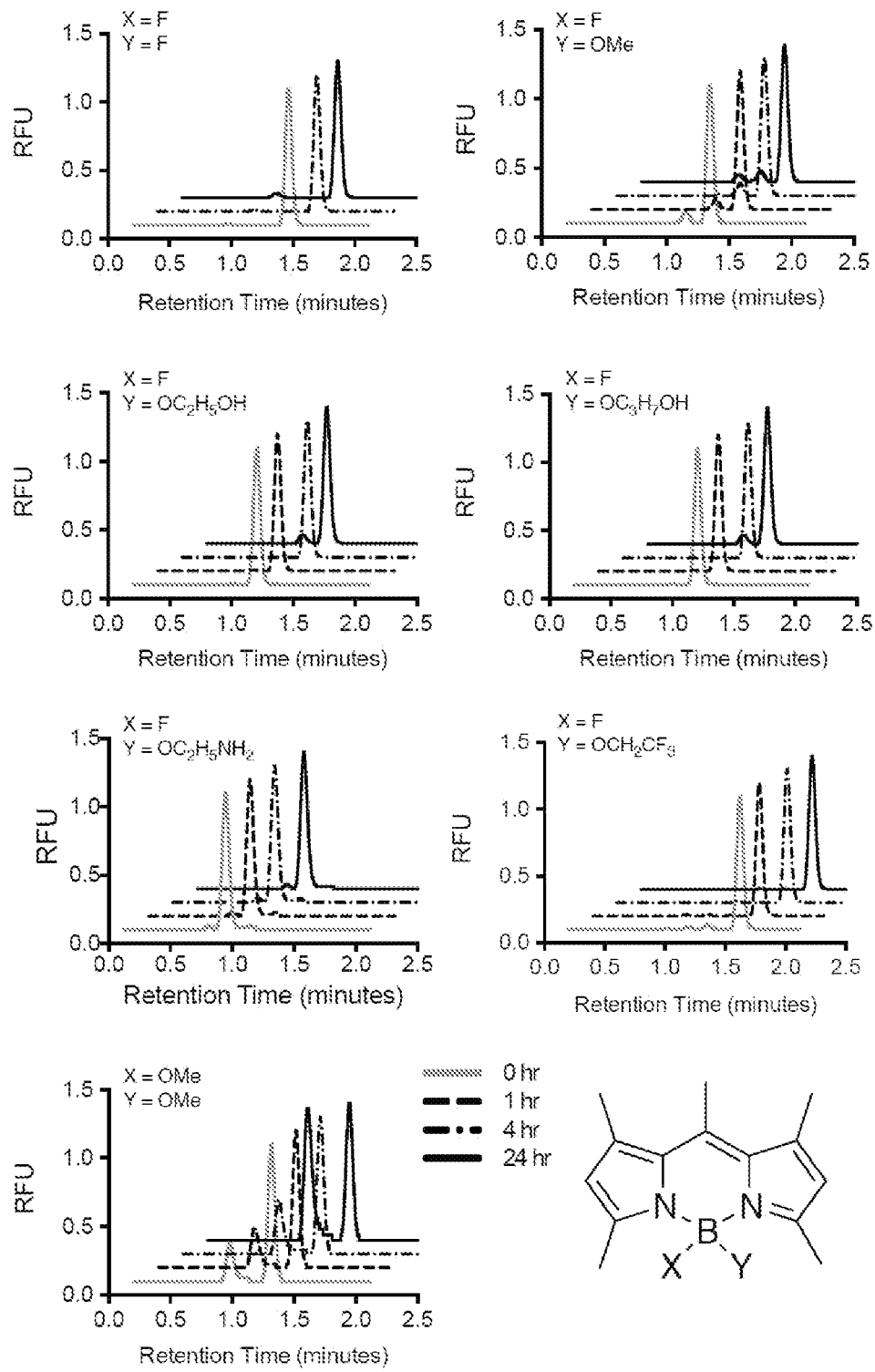
FIG. 3 shows the stability of mono-alkoxy BODIPY derivatives in aqueous solution at room temperature over 24 hours as monitored by LC/MS.
Figure 4:
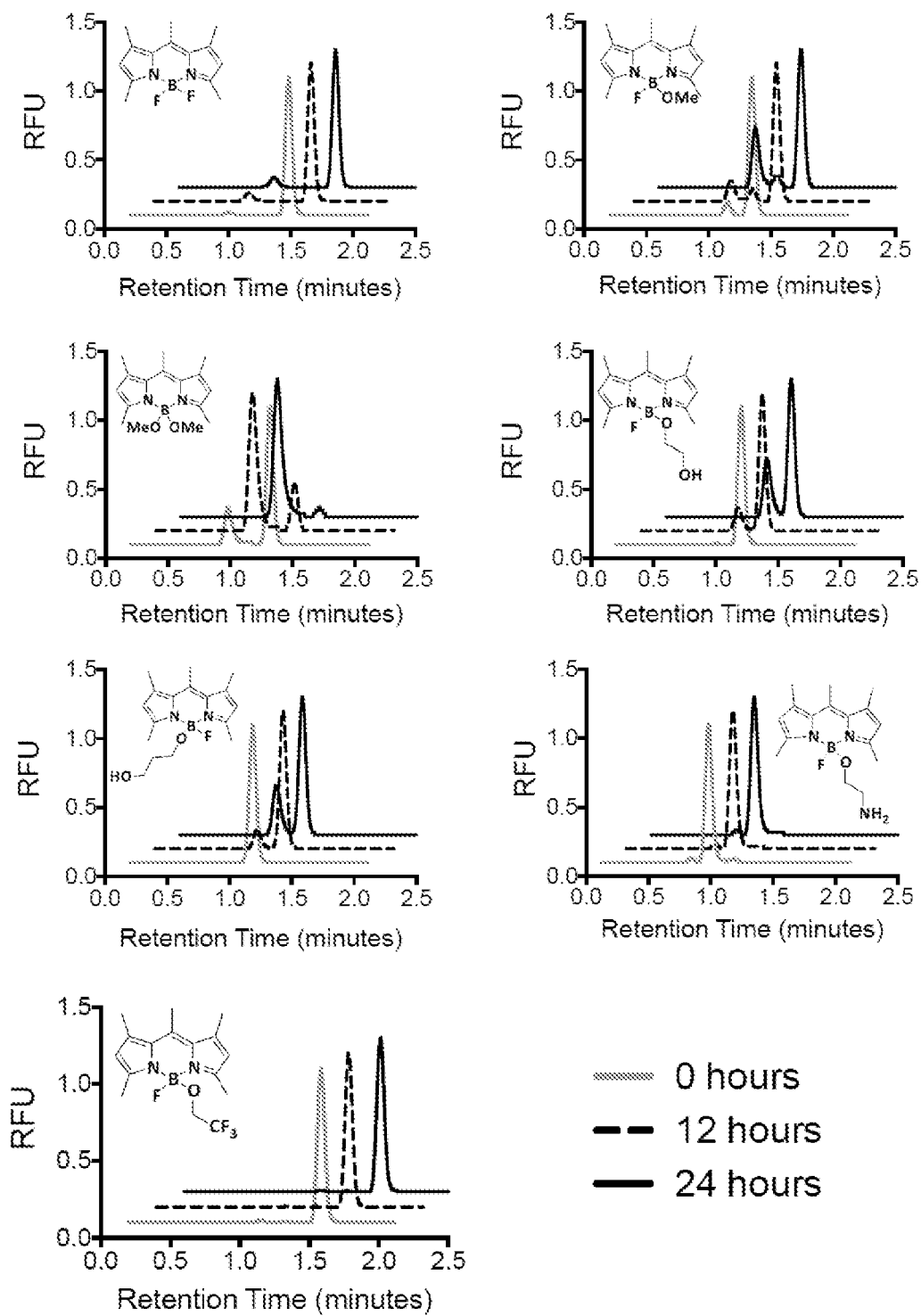
FIG. 4 shows the stability of mono-alkoxy BODIPY derivatives in aqueous solution at 37° C. over 24 hours as monitored by LC/MS.

The room-temperature (FIG. 3) and 37° C. (FIG. 4) data show consistent while not altogether predictable trends. First, all classes of BODIPY analogues investigated on the LC/MS—B—F$_2$, B—(OR)$_2$, B—F, (OR)— lead to one key type of fluorescent degradation product. This new product was found to be a hydroxy B—F, (OH) or B—(OR), (OH) adduct. All of these byproducts have retention times of approximately 0.7 minutes, and as such, they have distinguishable, chromatographic peaks from all parent BODIPY analogues. In the stability studies, the B—(OR)$_2$ analog performs poorly by undergoing nearly quantitative degradation to the hydroxy byproduct after 24 hours incubation at 37° C. This data stands in comparison to the mono-alkoxy derivatives that showed less than 50% degradation over the same time period.

Example 12

CDI Coupling of AMC1029

To AMC1029 (1 eq) in CH$_2$Cl$_2$ was added 1,1'-Carbonyldiimidazole (CDI; 25 eq) in CH$_2$Cl$_2$ (see, e.g., Wang, X.; Imber, B. S.; Schreiber, S. L. Bioconjugate Chem. 2008, 19, 585-587). After one hour under stirring at room temperature, CDI activation was complete and the reaction was quenched with 1:1 MeCN:H$_2$O. After 30 minutes, all solvents were removed in vacuo and the crude residue was dissolved in CH$_2$Cl$_2$. As a test primary amine, benzylamine (50 eq) was added under stirring at room temperature and complete conversion to the desired product was observed.

Example 13

TCO-Tetrazine Cycloaddition Reaction

Stock solutions of AMC1090 (20 μM) and trans-cyclooctene alcohol (TCO-alcohol; 40 μM) were prepared in 1×PBS (pH=7.3). AMC1090 (1 eq) and TCO-alcohol (2 eq) were mixed and reaction progress was monitored by LC/MS and via plate reader under kinetic and endpoint fluorescence readings tuned to the BODIPY wavelength ($\lambda_{exc}$=490 nm, $\lambda_{emm}$=512 nm).

Example 14

Cell Culture Studies

A. Cell Culture.

To investigate the impact of dye lipophilicity in the in vivo imaging context, we further treated MD-MBA 231 cells (with an H2B mCherry fluorescent reporter to localize the nucleus) with each compound for 24 hours at 10 μM, 1 μM, and 100 nM. Cells (MDA-MB-231 pLVX H2B-mCherry) lines were cultured using sterile technique in plastic dishes with standard cell-growth media [RPMI 1640 1× (+) phenol red, (+) 10% FBS, (+) 1% Pen-Strep]. Culture incubation during and in between experiments was performed in a sterile incubator (37° C., 5% CO$_2$). All cultures used in imaging studies were confirmed to be mycoplasma-free prior to experimentation using a commercially available detection kit (MycoAlert, Lonza).

Figure 5:
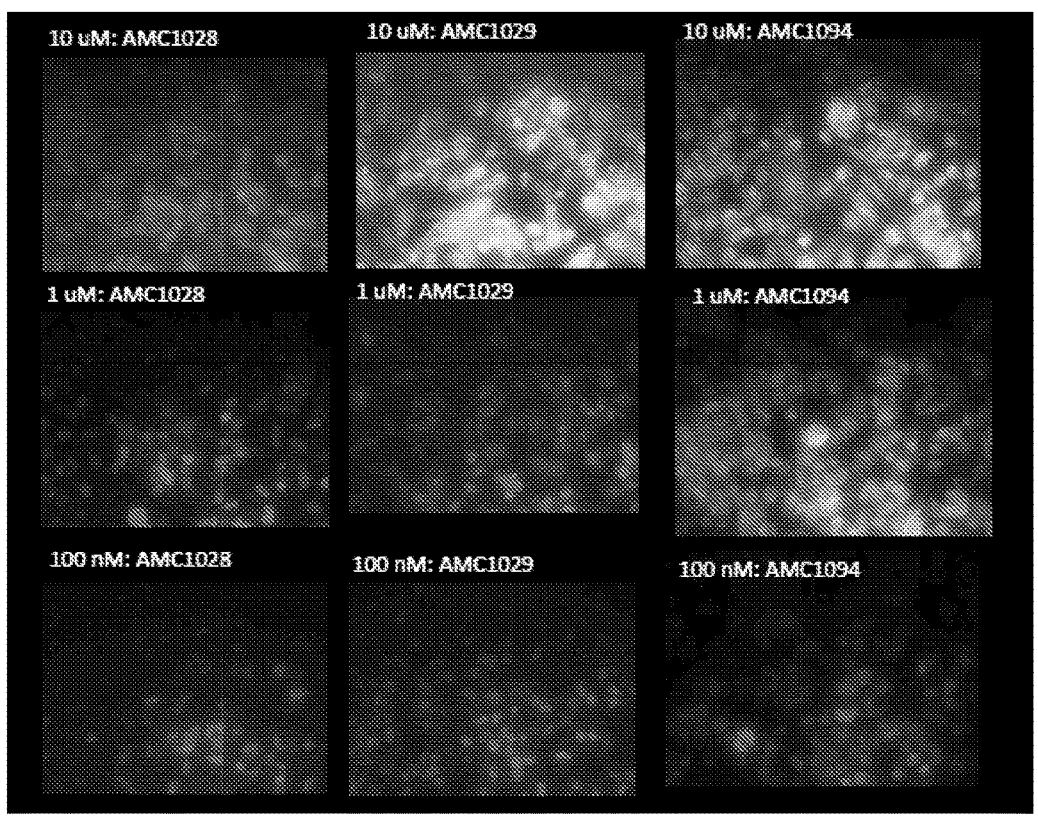
FIG. 5 shows representative fluorescence imaging data of compounds AMC1028, AMC1029, and AMC1094 after removal of spent media and exchange with a thin layer of clear imaging media.

FIG. 5 shows representative fluorescence imaging data of these compounds on live cells after removal of spent media and exchange with thin layer of clear imaging media. AMC1028 and AMC1029 show diffuse fluorescent signal as expected for cells treated with a core fluorophore lacking any targeting element. By contrast, the difluoro analogue AMC1094, engages in significant non-specific staining of cellular compartments. These findings show that the mono-alkoxy derivatives can produce bright staining of live cells with the benefit of easily diffusing in and out of the cell and its organelles. This property thereby limits non-specific staining effects that could have a confounding effect small-molecule imaging applications.

B. Live Cell Imaging.

Further validation of the dyes' low-lipophilicity was achieved via a wash-out experiment with the MD-MBA 231 cell line. In this experiment, we investigated the ease of washing out the mono-alkoxy fluorophores within 30 minutes (e.g., within 15 minutes of the start of incubation).

Two days prior to imaging, cells were seeded at 20,000 cells/well on a 96-well Glass Bottom Microwell plate (MatriPlate, MGB096-1-2-LG-L) treated with 1× Attachment Factor (0.1% gelatin, Gibco). For these experiments, phenol-red free imaging media was used [RPMI 1640 1× (+) 10% FBS]. The day of imaging, each well was incubated for 30 minutes with 10 M of the title compound suspended in cell imaging media (final DMSO content=0.1%). Subsequently three washes were performed. Each wash consisted of removing spent media, adding fresh imaging media, and incubating the cells for 30 minutes. After the final wash, the media was aspirated, a thin layer of cell imaging media was added, and wells were rapidly imaged.

Live-cell imaging was performed on a Zeiss Axiovert 100M inverted epifluorescence microscope with a 40× objective. Per region of interest, a bright field view was acquired as well as GFP, TexasRed fluorescence channels.

Figure 6:
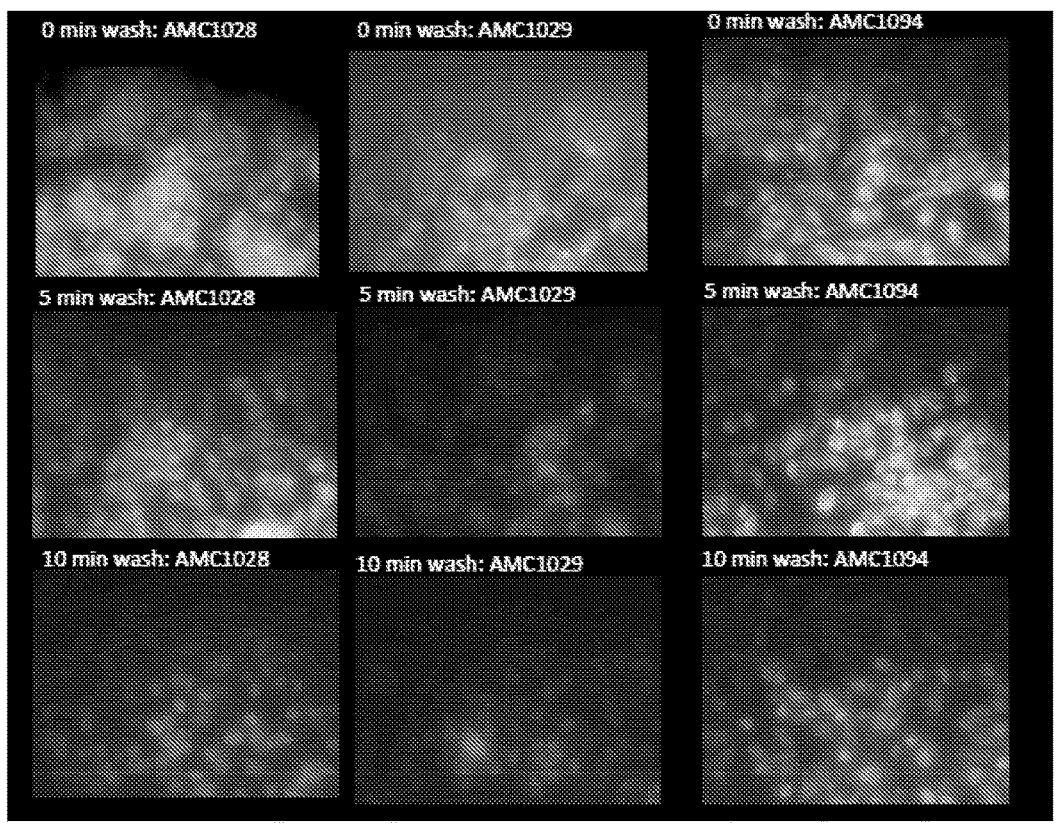
FIG. 6 illustrates the representative fluorescence imaging data of compounds AMC1028, AMC1029, and AMC1094 following a short incubation and subsequent washing of the cells.

The data in FIG. 6 demonstrate the facile efflux of the mono-alkoxy derivatives in stark contrast to the persistent non-specific staining of the difluoro control compound AMC1094. This lends further support to the benefit of using an alkoxy BODIPY over a traditional difluoro-analogue.

Example 15

Preparation of 10-(2-carboxyethyl)-5-fluoro-1,3,7,9-tetramethyl-5-(oxetan-3-yloxy)-5H-dipyrrolo[1,2-c:2',1'-f][1,3,2]diazaborinin-4-ium-5-uide (MS46) and 10-(2-carboxyethyl)-1,3,7,9-tetramethyl-5,5-bis(oxetan-3-yloxy)-5H-dipyrrolo[1,2-c:2',1'-f][1,3,2]diazaborinin-4-ium-5-uide (MS47)

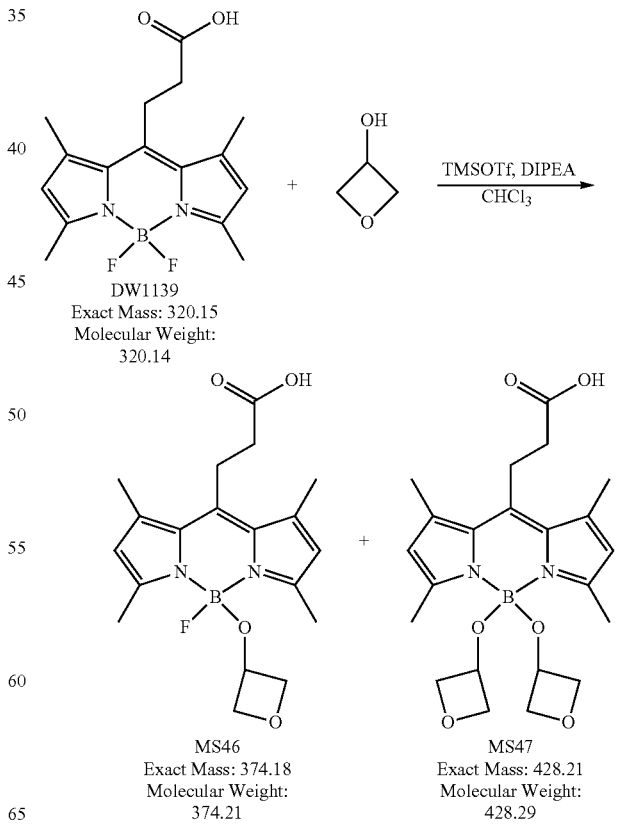

DW1139 (24.3 mg/76.3 µmol/1 eq) was dissolved in 8 mL CHCl₃ (anhyd.). TMSOTf (68.7 µL/84 mg/0.38 mmol/5 eq) dissolved in 700 µL CHCl₃ (anhyd.) was carefully added to the BODIPY solution at room temperature. After 5 min, 3-hydroxyocetane (241 µL/281 mg/3.8 mmol/50 eq) was added. One minute later, DIPEA (132 µL/98 mg/0.76 mmol/10 eq) was added. After 3 min, the crude reaction mixture was partitioned between 60 mL brine/2-Methyl-THF (1:1). The organic phase was washed twice with brine. Combined aqueous phases were acidified with HCl (pH 3) and extracted twice with 2-methyl-THF. Combined organic phases were then dried over MgSO₄ and filtered. The solvent was removed in vacuo. The crude products were purified by column chromatography. Pure fractions were combined and solvent removed in vacuo. Product was an orange powder.

Example 16

Preparation of 5-fluoro-1,3,7,9,10-pentamethyl-5-(oxetan-3-yloxy)-5H-dipyrrolo[1,2-c:2',1'-f][1,3,2]diazaborinin-4-ium-5-uide (MS43) and 1,3,7,9,10-pentamethyl-5,5-bis(oxetan-3-yloxy)-5H-dipyrrolo[1,2-c:2',1'-f][1,3,2]diazaborinin-4-ium-5-uide (MS44)

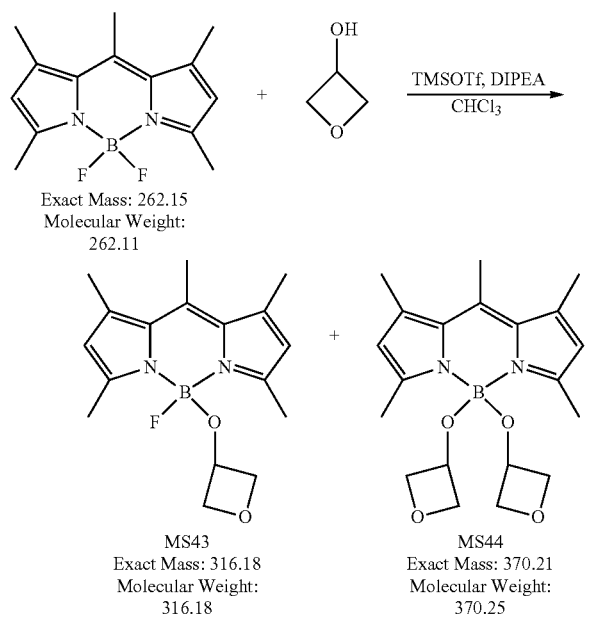

Pentamethyl-BODIPY (60 mg/0.23 mmol/1 eq) was dissolved in 25 mL CHCl₃ (anhyd.). TMSOTf (206 µL/252 mg/1.15 mmol/5 eq) was dissolved in 2 mL CHCl₃ (anhyd.) and carefully added to the BODIPY solution at room temperature. After 7 min, a mixture of DIPEA (400 µL/294 mg/2.28 mmol/10 eq) and 3-Hydroxyoxetane (300 µL/351 mg/4.74 mmol/20 eq) was added. After 5 min, the crude reaction mixture was partitioned between 60 mL brine/2-Methyl-THF (1:1). The organic phase was washed twice with brine. Organic phase dried over MgSO₄ and filtered. Solvent was removed in vacuo. Crude product was then purified by column chromatography using a gradient of 10%→70% acetonitrile in toluene. Pure fractions were combined and the solvent removed in vacuo. Product yielded as an orange powder. Yield MS43: 21.1 mg/0.067 mmol/29%; Yield MS44: 5.4 mg/0.015 mmol/6.5%.

Example 17

Preparation of 5-acetoxy-5-fluoro-1,3,7,9,10-pentamethyl-5H-dipyrrolo[1,2-c:2',1'-f][1,3,2]diazaborinin-4-ium-5-uide (MS76)

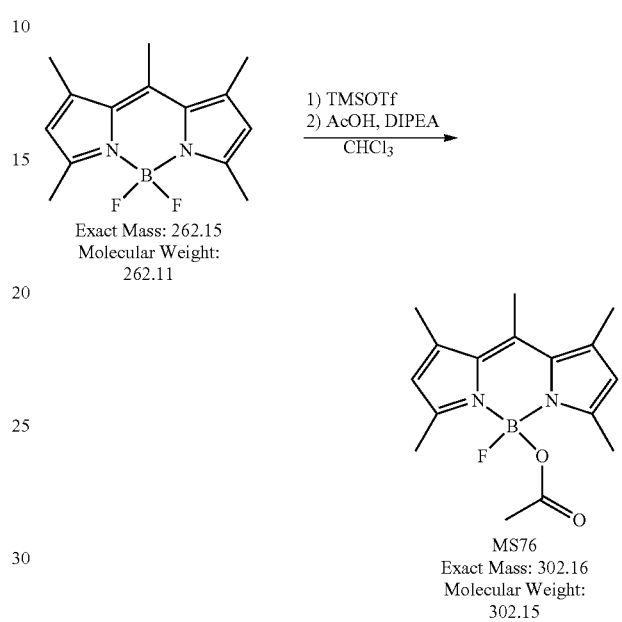

Pentamethyl-BODIPY (60 mg/0.23 mmol/1 eq) was dissolved in 20 mL CHCl₃ (anhyd.). The solution was stirred at 0° C. TMSOTf (68.7 µL/84 mg/0.38 mmol/5 eq) was dissolved in 700 µL CHCl₃ (anhyd.) and carefully added to the BODIPY solution under vigorous stirring. After 2:30 min, a mixture of DIPEA (174 µL/1.00 mmol/13 eq) and AcOH (87.4 µL/1.53 mmol/20 eq) was added quickly and the reaction mixture was allowed to warm to room temperature. After 3 min, the reaction was quenched by adding 5 mL H₂O. The crude reaction mixture was partitioned between 100 mL H₂O/DCM (1:1). The organic phase was washed three times with brine/H₂O and dried over Na₂SO₄. The solvent was removed in vacuo and the crude product was purified by column chromatography over neutral alumina column using a gradient of 0%→100% acetonitrile in toluene. Product yielded as orange powder. Yield: 8.2 mg/27.2 µmol/36%.

Example 18

Preparation of

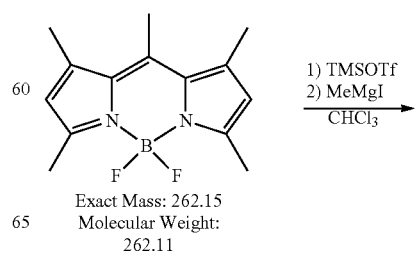

-continued

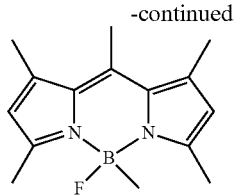
MS77
Exact Mass: 258.17
Molecular Weight: 258.15

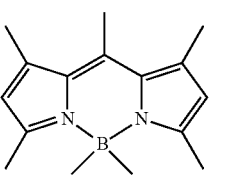
MS77b
Exact Mass: 254.20
Molecular Weight: 254.18

Pentamethyl-BODIPY (60 mg/0.23 mmol/1 eq) was dissolved in 20 mL CHCl₃ (anhyd.). Solution was stirred at 0° C. TMSOTf (68.7 μL/84 mg/0.38 mmol/5 eq) was dissolved in 700 μL CHCl₃ (anhyd.) and carefully added to the BODIPY solution under vigorous stirring. After 2:30 min, 3M MeMgI in THF (333 μL/1.00 mmol/13 eq) was added and the reaction mixture was allowed to warm to room temperature. After 3 min, the reaction was quenched by adding 5 mL H₂O. The crude reaction mixture was partitioned between 100 mL H₂O/DCM (1:1). The Organic phase was washed three times with brine/H₂O and dried over Na₂SO₄ and filtered. The solvent was removed in vacuo and the crude product was purified by column chromatography over neutral alumina column using a gradient of hexanes/toluene (1:1)→100% toluene→100% acetonitrile. Product yielded as an orange powder. Yield MS77 (mono product): 2.7 mg/10.5 μmol/14%. Yield MS77b (bis product): 16.0 mg/63.0 μmol/83%.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I):

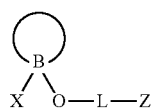

wherein:

is a BODIPY ligand system;
X is $^{18}F$ or $^{19}F$;
L is absent or a linker; and
Z is selected from the group consisting of: a group reactive with a biologically active molecule and a detectable agent;
wherein the moiety O-L-Z is selected from the group consisting of:

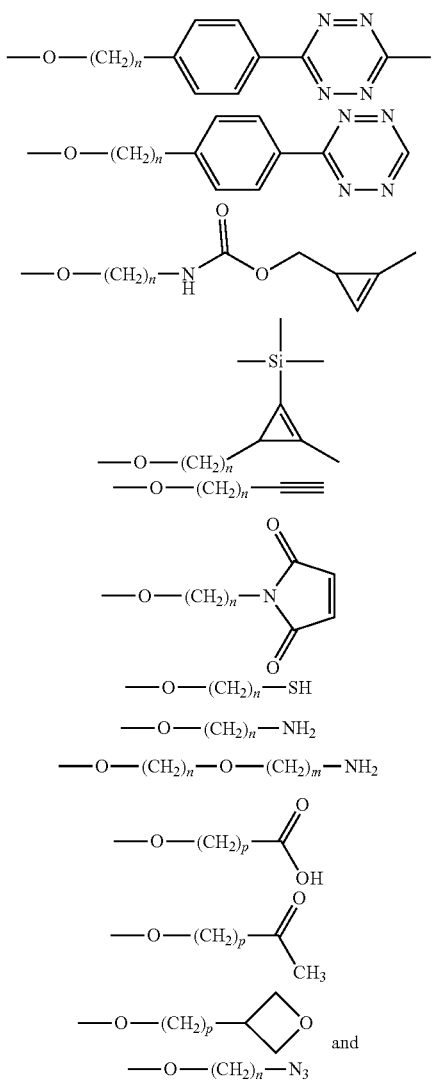

wherein n and m are independently an integer from 1 to 20; and p is an integer from 0 to 20.

2. A compound of Formula (II):

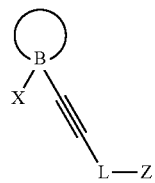

wherein:

is a BODIPY ligand system;

X is $^{18}$F or $^{19}$F;

L is absent or a linker; and

Z is selected from the group consisting of: a group reactive with a biologically active molecule and a detectable agent;

wherein the moiety $(C_2)$-L-Z is selected from the group consisting of:

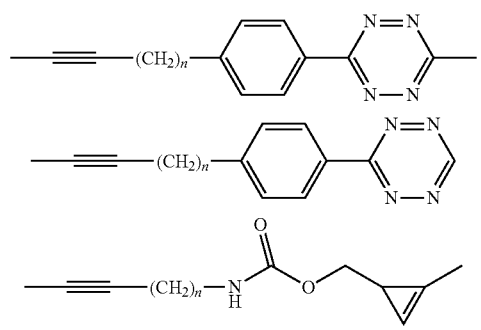

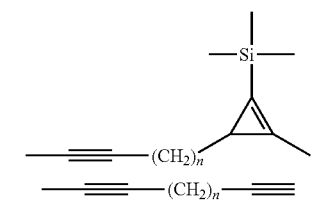

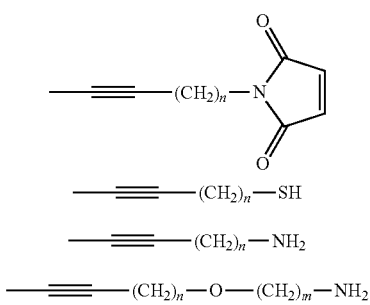

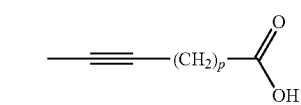

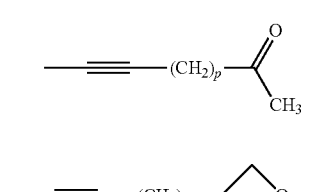

wherein n and m are each independently an integer from 1 to 20, and p is an integer from 0 to 20.

3. The compound of claim 1, wherein X is $^{18}$F.

4. A compound selected from the group consisting of:

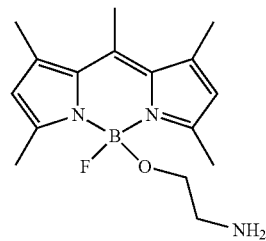

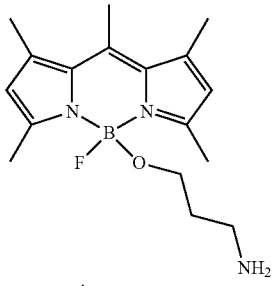

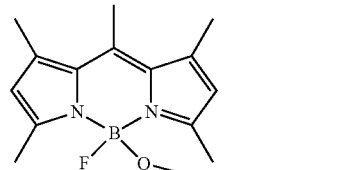

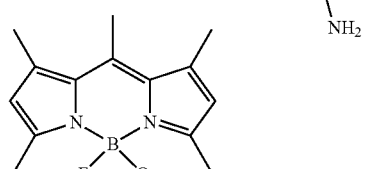

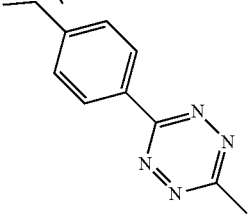

and

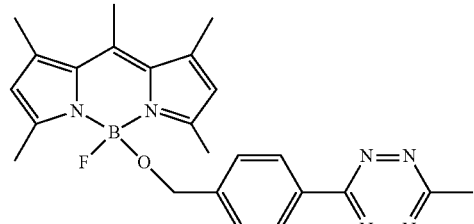

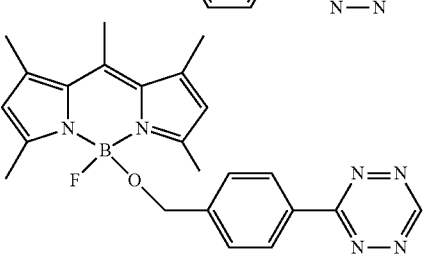

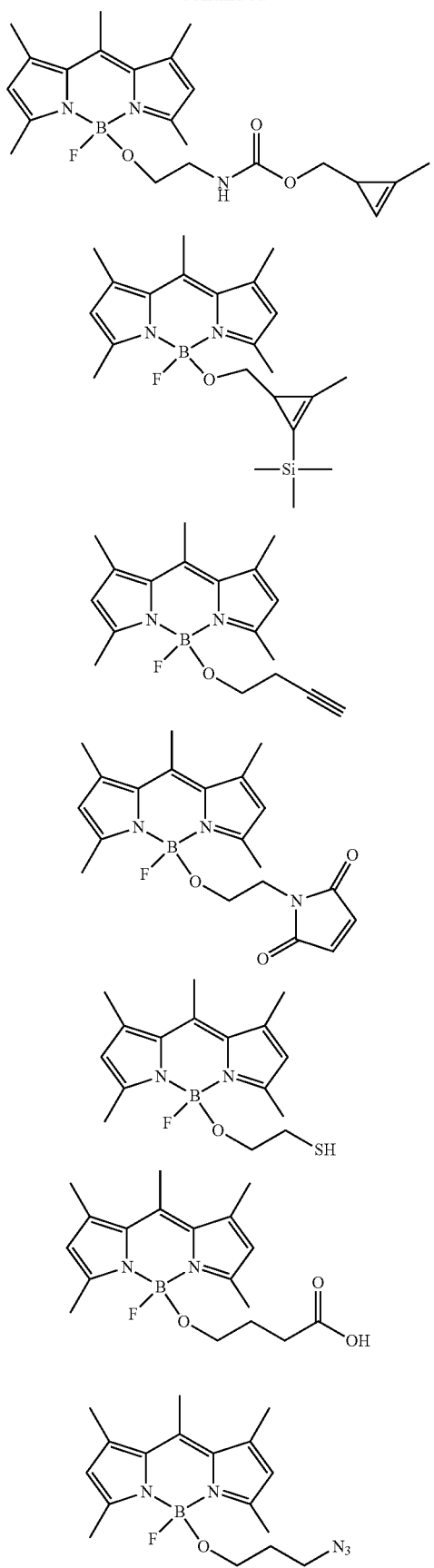
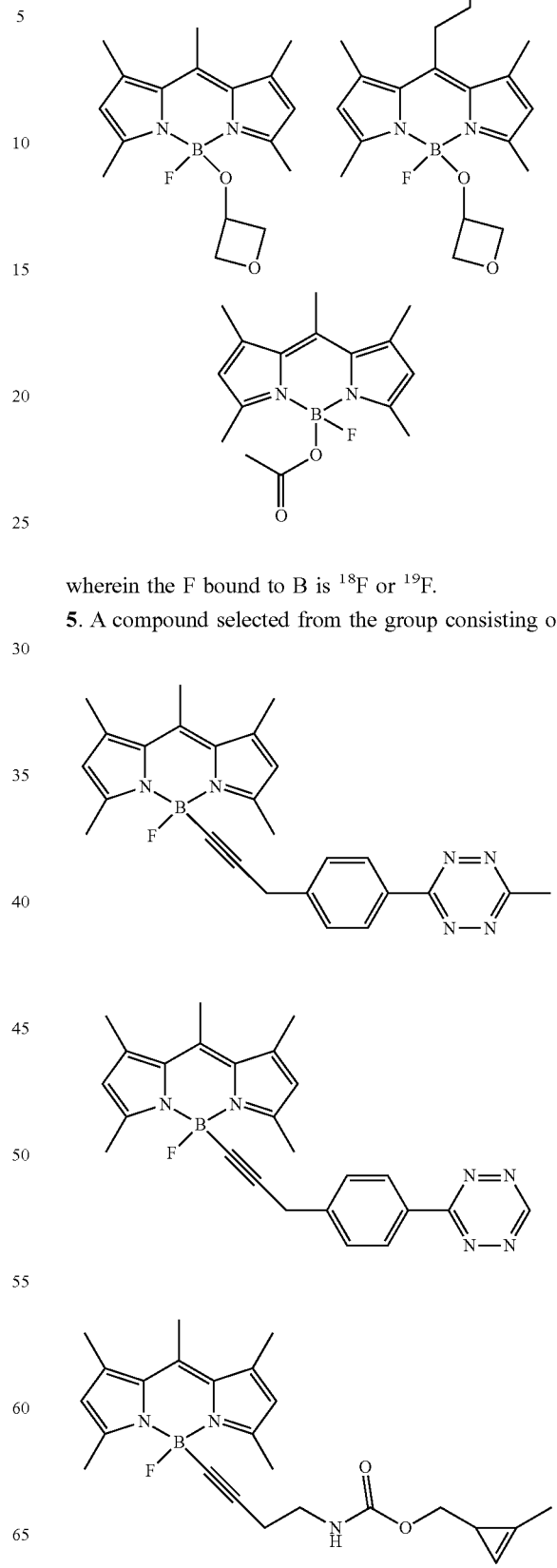
wherein the F bound to B is $^{18}$F or $^{19}$F.
5. A compound selected from the group consisting of:

-continued

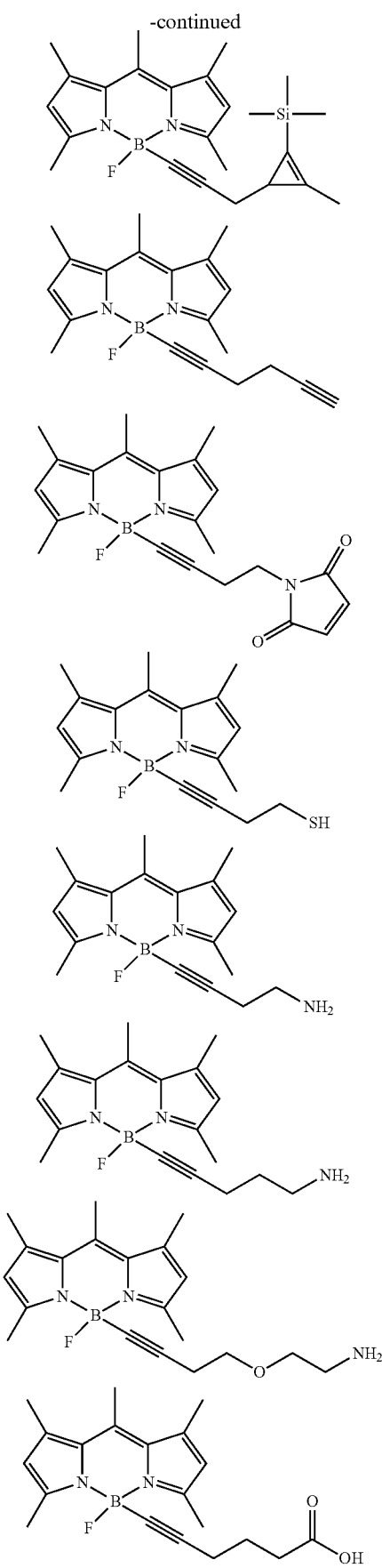

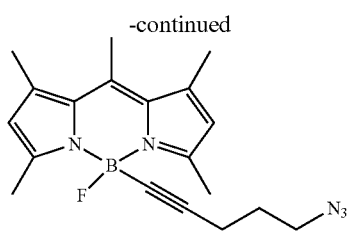

wherein the F bound to B is $^{18}$F or $^{19}$F.

6. A compound of Formula (III):

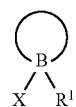

wherein:

is a BODIPY ligand system selected from the group consisting of:

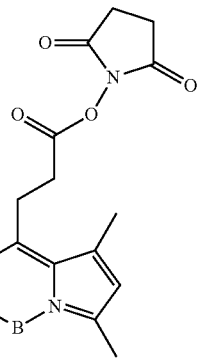

X is $^{18}$F or $^{19}$F; and

R$^1$ is selected from the group consisting of: a substituted or unsubstituted C$_{1-20}$ alkyl, substituted or unsubstituted C$_{1-20}$ alkoxy, or substituted or unsubstituted C$_{1-20}$ alkynyl.

7. A compound of Formula (VII):

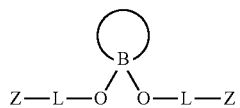

wherein:

is a BODIPY ligand system; and
each L-Z is
8. The compound of claim 7, wherein the compound of Formula (VII) is selected from the group consisting of:
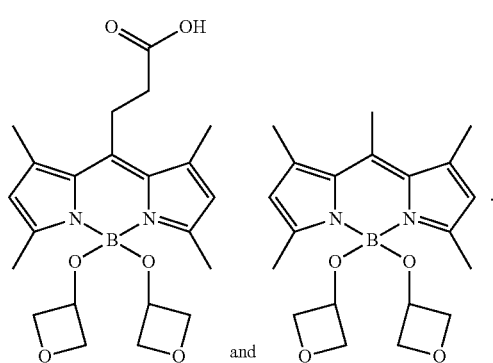
and
* * * * *

UNITED STATES PATENT AND TRADEMARK OFFICE
CERTIFICATE OF CORRECTION

PATENT NO. : 10,005,793 B2  
APPLICATION NO. : 14/432567  
DATED : June 26, 2018  
INVENTOR(S) : Ralph Mazitschek, Alexandra M. Courtis and James Adam Hendricks Page 1 of 1

It is certified that error appears in the above-identified patent and that said Letters Patent is hereby corrected as shown below:

On the Title Page

Column 1, (Notice), Line 14, after "0 days." delete "days."

Signed and Sealed this  
Eighteenth Day of February, 2020

Andrei Iancu  
*Director of the United States Patent and Trademark Office*